US007163788B2

(12) United States Patent
Tong

(10) Patent No.: US 7,163,788 B2
(45) Date of Patent: Jan. 16, 2007

(54) METHOD OF DETECTING MOLECULAR TARGET BY PARTICULATE BINDING

(76) Inventor: Sun-Wing Tong, 1519 Frish Moss Ct., Bakersfield, CA (US) 93311

( * ) Notice: Subject to any disclaimer, the term of this patent is extended or adjusted under 35 U.S.C. 154(b) by 479 days.

(21) Appl. No.: 10/291,986

(22) Filed: Nov. 12, 2002

(65) Prior Publication Data
US 2003/0215825 A1 Nov. 20, 2003

(30) Foreign Application Priority Data
Apr. 9, 2002 (AU) .................................. PS1597

(51) Int. Cl.
  *C12Q 1/68* (2006.01)
  *C07H 21/02* (2006.01)
  *C07H 21/04* (2006.01)
(52) U.S. Cl. .................. 435/6; 536/23.1; 536/24.3
(58) Field of Classification Search .............. 435/6, 435/7.1; 530/300, 350, 391.1; 536/23.1, 536/24.3
See application file for complete search history.

(56) References Cited

U.S. PATENT DOCUMENTS

| 4,895,796 A * | 1/1990 | Lanier et al. ............... 435/7.24 |
| 6,342,349 B1 * | 1/2002 | Virtanen ......................... 435/6 |
| 6,506,564 B1 * | 1/2003 | Mirkin et al. .................... 435/6 |
| 6,579,721 B1 * | 6/2003 | Natan et al. .................. 436/164 |
| 2002/0052042 A1 * | 5/2002 | Gordon ..................... 435/287.2 |
| 2003/0003464 A1 | 1/2003 | Phan et al. |
| 2003/0175740 A1 * | 9/2003 | Mullinax et al. ............... 435/6 |
| 2003/0194704 A1 * | 10/2003 | Penn et al. ...................... 435/6 |

FOREIGN PATENT DOCUMENTS

| WO | WO 02/42498 | 5/2002 |
| WO | WO 03/087827 | 10/2003 |

OTHER PUBLICATIONS

K. A. Schouhamer Immink, "The Compact Disc Story", J. Audio Eng. Soc., vol. 46, No. 5, May 1998, pp. 458-465.
D. Y. Zhang et al., "Amplification of Target-Specific, Ligation-Dependent Circular Probe", Gene 211 (1998), pp. 277-285.
D. Y Zhang et al., "Ramification Amplification: A Novel Isothermal DNA Amplification Method", Molecular Diagnosis, vol. 6, No. 2, 2001, pp. 141-150.
D. Y. Zhang et al., "Detection of Rare DNA Targets by Isothermal Ramification Amplification", Gene 74 (2001), pp. 209-216.
R. M. Umek, et al., "Electronic Detection of Nucleic Acids *A Versatile Platform for Molecular Diagnostics*", Journal of Molecular Diagnostics, vol. 3, No. 2, May 2001, pp. 76-84.
So-Jung Park et al., "Array-Based Electrical Detection of DNA with Nanoparticle Probes", Science, vol. 295, Feb. 22, 2002, pp. 1503-1506.
D. R. Baselt et al., "A Biosensor Based on Magnetoresistance Technology", Biosensors & Bioelectronics 13, 731-739 (1998), pp. 1-12.

D. R. Baselt et al., "A High-Sensitivity Micromachined Biosensor", Proc. IEEE 85 (4), 672-680 (1997), pp. 1-16.
M. S. Behr et al., "Transmission of *Mycobacerium Tuberculosis* From Patients Smear-Negative for Acid-Fast Bacilli", The Lancet, vol. 353, Feb. 6, 1999, pp. 444-449.
J. S. Bergmann et al., "Clinical Evaluation of the Enhanced Gen-Probe Amplified Mycobaterium Tuberculosis Direct Teest for Rapid Diagnosis of Tuberculosis in Prison Inmates", Journal of Clinical Microbiology, vol. 37. No. 5, May 1999, pp. 1419-1425.
J. S. Bergmann, et al., "Enhanced Mycobacterium Tuberculosis Direct Test for Detection of M. Tuberculosis Comples in Positive ESP II Browth Cultures of Nonrespiratory Specimens", Elsevier, pp. 245-248.
P. Chedore et al., "Routine Use of the Gen-Probe MTD2 Amplification Test for Detection of *Mycobacterium tuberculosis* in Clinical Specimens in a Large Public Health Mycobacteriology Laboratory", Elsevier, pp. 186-191.
P. Della-Latta et al., "Comprehensive Evaluation of Performance, Laboratory Application, and Clinical Usefulness of Two Direct Amplification Technologies for the Detection of *Mycobacterium tuberculosis* Complex", Microbiology and Infectious Disease, American Journal of Clinical Pathology, 1998, 110, pp. 301-310.
P. Della-Latta et al., "Inhibitory Effect of Alpha-Tec XPR-Plus Phosphate Buffer on the Enhanced Gen-Probe Amplified Mycobacterium Tuberculosis Direct Test", Journal of Clinical Microbiology, Apr. 1999, vol. 37, No. 4, pp. 1234-1235.
F. Gamboa et al., "Comparative Evaluation of Initial and New Versions of the Gen-Probe Amplified Mycobacterium Tuberculosis Direct Test for Direct Detection of Mycobacterium tuberculosis in Respiratory and Nonrespiratory Specimens", Journal of Clinical Microbiology, Mar. 1998, vol. 36, No. 3, pp. 684-689.
D. F. Moore et al., "AMPLIFIED™ Mycobacterium Tuberculosis Direct Test", pp. 1-2.
C. Piersimoni et al., "Comparative Evaluation of the New Gen-Probe *Mycobacterium tuberculosis* . . . ", Journal of Clinical Microbiology, Dec. 1998, pp. 3601-3604, vol. 36, No. 12.
S. X. Wang et al., "Evaluation of Three Nucleic Acid Amplification Methods for Direct Detection of Mycobacterium tuberculosis Complex in Respiratory Specimens", Journal of Clinical Microbiology, Jun. 1999, vol. 37, No. 6, pp. 1932-1934.
A. J. Bakker et al., "Troponin T and Myoglobin at Admission: Value of Early Diagnosis of Acute Myocardial Infarction", European Heart Journal (1994) 15, pp. 45-53.
R. J. de Winter Abstract "Value of Myoglobin, Troponin T. and CK-MB sub mass in Ruling Out an Acute Myocardial Infarction in the Emergency Room", Circulation, vol. 92 (12), Dec. 15, 1995, 3401-3407.

(Continued)

*Primary Examiner*—Ethan Whisenant
(74) *Attorney, Agent, or Firm*—Cohen, Pontani, Lieberman & Pavane

(57) ABSTRACT

A method of detecting or quantifying a molecular target in a sample utilizing the molecular interaction between molecular targets, bead-bound probes, and support-bound probes. Laser light or a magnetic sensor may be used to detect the beads after the interaction. The detection of the beads indicates the presence of the molecular target in the sample.

34 Claims, 24 Drawing Sheets

OTHER PUBLICATIONS

C.W. Hamm, et al., "New Biochemical Markers for Myocardial Cell Injury", Current Opinion in Cardiology, 1995, 10:355-360.

J. F. Tucker et al, "Value of Serial Myoglobin Levels in the Early Diagnosis of Patients Admitted for Acute Myocardial Infarction", Annals of Emergency Medicine 24:4, Oct. 1994, pp. 704-708.

P. Brown et al., "Bovine Spongiform Encephalopathy and Variant Creutzfeldt-Jakob Disease: Background, Evolution, and Current Concerns", Perspectives, vol. 7, No. 1, Jan-Feb. 2001.

J. Bieschke et al., "Ultrasenstive Detection of Pathological Prion . . . ", PNAS, May 9, 2000, vol. 97, No. 10. pp. 5468-5473.

M. R. Scott et al., "Identification of a Prion Protein Epitope Modulating . . . ", Proc. Natl. Acad. Sci., vol. 94, pp. 14279-14284, Dec. 1997.

J. Moynagh et al., The Evaluation of Tests for the Diagnosis of Transmissible Spongiform Encephalopathy in Bovines, Jul. 8, 1999, pp. 1-36.

J. Safar et al., "Eight Prion Strains have $PrP^{sc}$ Molecules with Different Conformations", Nature Medicine, vol. 4, No. 10, Oct. 1998, pp. 1157-1165.

BSE Surveillance, U.S. Department of Agriculture, Animal and Plant Health Inspection Service, Internet publication link: http://www.aphis.usda.gov/oa/bse.

G. Traverso et al., Detection of *APC* Mutations in Fecal DNA from Patients with Colorectal Tumors, N. Engl J Med 2002; 346:311-320, Jan. 31, 2002.

\* cited by examiner

FIG. 3
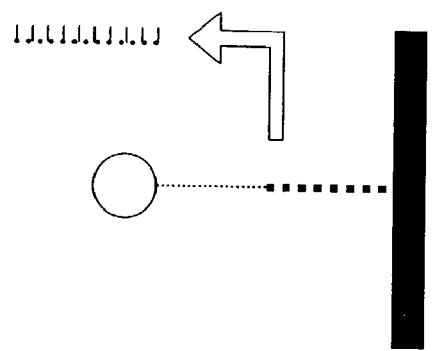
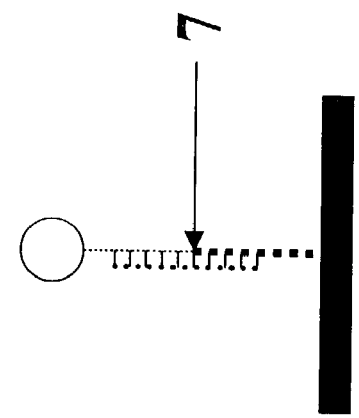
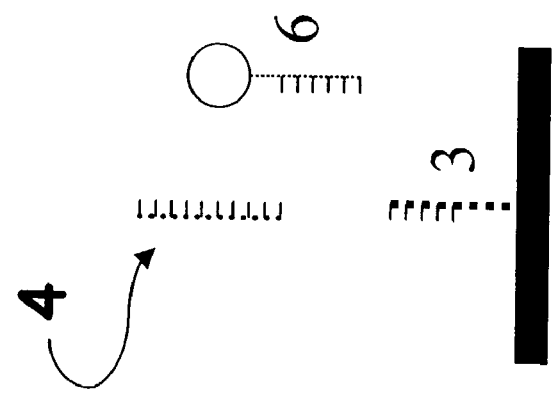

FIG. 6A 10001011010101 01001001111010 10101100101101
    A                     N                   T 10101001000101 00101011011010 10001011010101
    H                     R                   A 11000100110010  11001011000100  N
    X              11011011010100  Y
                 Anthrax biochips [11]

FIG. 6B 10001011010101 01001001111010 10101100101101
    A                     N                   T 10101001000101 00101011011010 10001011010101
    H                     R                   A 11000100110010  10001011000100  N
    X              10011011010100  Y
               Anthrax biochips [11]
              10111011111100  Y FIG. 9A
Before
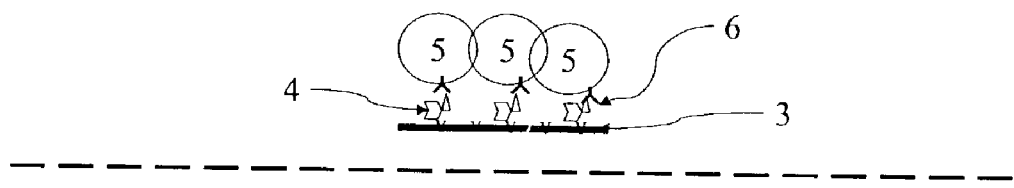
After
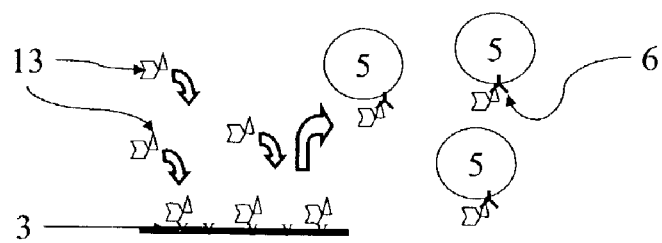
FIG. 9B
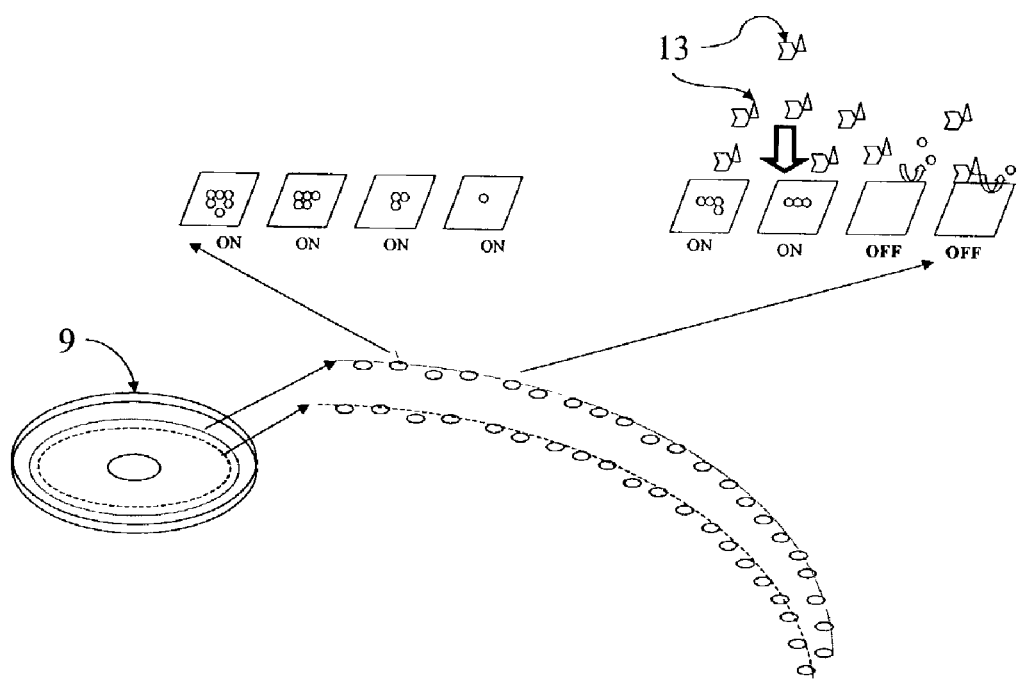

[ANALYTE] = K x signal $$[\text{ANALYTE}] = C \times \frac{1}{\text{signal}}$$

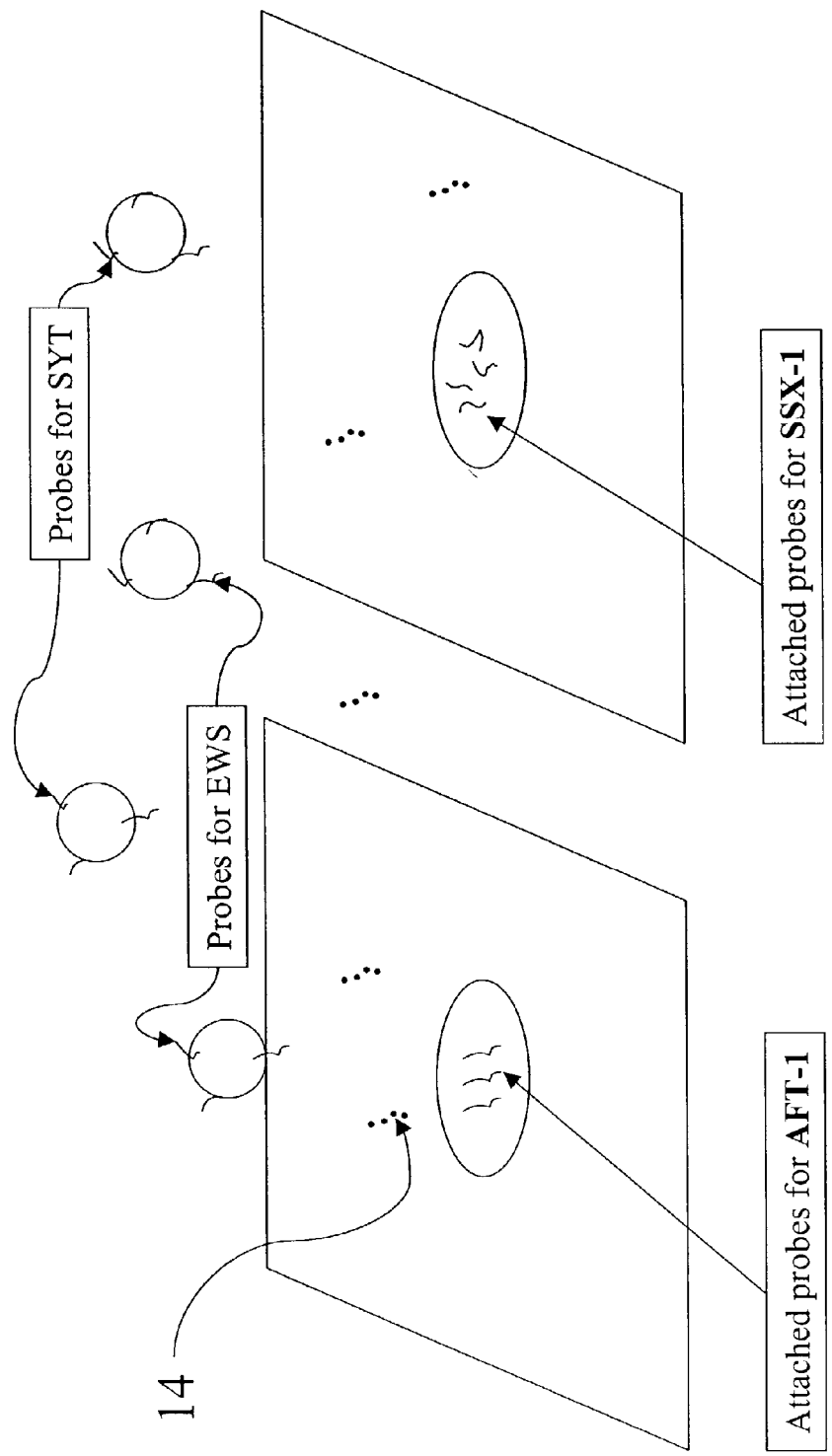

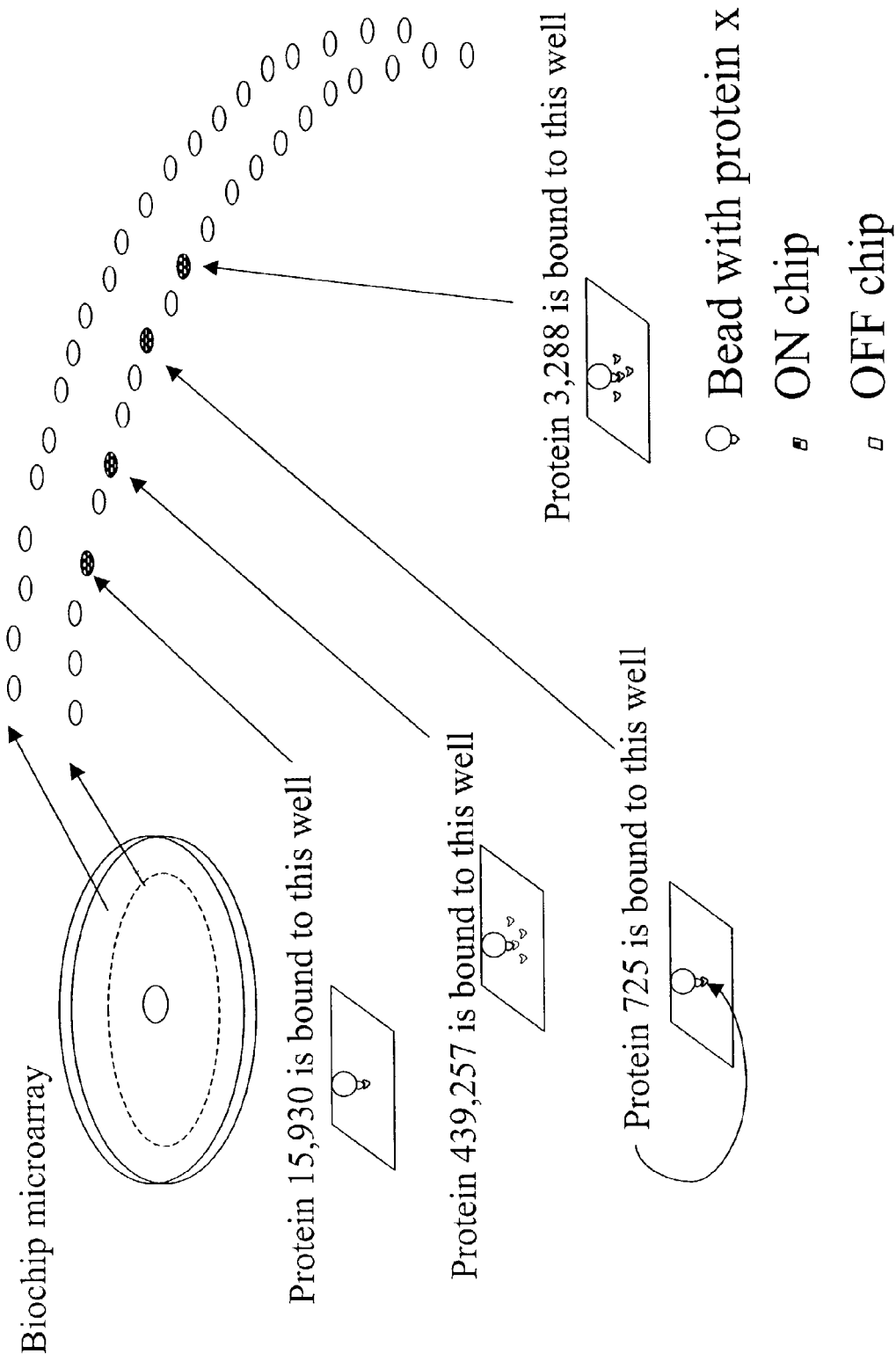

```
                             SEQUENCE LISTING

<160> NUMBER OF SEQ ID NOS: 7

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
ggtggcggct gttgctgctg ctg                                              23

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
tccttccagc agcagcagca acagccgcca cc                                    32

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
ggtggcggct gttgctgctg                                                  20

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
ggtggcggct gttgctgctg ctgctgctg                                        29

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
gttacgctta gcctagatcc ta                                               22
```

```
<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
gttacgctta gtctagatcc ta                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
taggatgtag actaagcgta ac                                              22
```

METHOD OF DETECTING MOLECULAR TARGET BY PARTICULATE BINDING

RELATED APPLICATIONS

This application claims priority from the Australian Provisional Application Number PS1597 which was filed on Apr. 9, 2002, the content of which is hereby incorporated by reference in its entirety.

BACKGROUND OF THE INVENTION

1. Field of the Invention

The present invention relates to the detection and quantification of specific molecular interactions such as nucleic acid hybridization, antigen-antibody reaction, receptor-ligand interaction and other specific molecular interactions through the use of small beads, preferably aggregated beads for ease of detection, and the detection by various physical and chemical means. This invention is widely applicable to medicine, industry—both civilian and defense, environmental monitoring and scientific research.

2. Description of the Related Art

Nucleic acid hybridization, antigen-antibody reaction and receptor-ligand binding are examples of molecular interactions, which because of the specificity of the interaction, are of tremendous value in the identification, or detection of these substances. Such specific molecular interactions can be detected by various means, with different sensitivities and specificities, involving target or signal amplifications. Amplification for antigen-antibody reaction is based on signal amplification, such as by enzymatic reaction. Nucleic acids can be detected by both signal amplification and target amplification through the polymerase chain reaction (PCR). Although PCR is extremely sensitive, it is laborious and not consistently precise. Additionally, because PCR requires multiple cycles of melting, annealing and extension, it needs to take at least one hour. Recently, real-time PCR has improved the endpoint detection, thereby reducing the period to accomplish the process. Nevertheless, cycling is still required. In addition, techniques that enhance the sensitivity and specificity of target nucleic acid amplification in an isothermal environment have been introduced.

Hence, it is desirable to develop a simple, inexpensive process and apparatus which can eliminate the need for target amplification and to speed up the overall process of detection of molecular targets.

SUMMARY OF THE INVENTION

This invention provides methods of detecting or identifying trace quantities of molecular targets, and measuring the concentration of biological molecules in solution. These methods are based on the specific affinity of macromolecules to each other, such as Watson-Crick binding between complementary nucleic acid molecules and antigen-antibody binding.

According to the invention, a pair of probes showing high avidity and specificity for a molecular target are synthesized. One of the pair is bound to a solid surface and the other is attached to particles ("beads") made of various materials, preferably ferromagnetic and metallic. The beads are either soluble or insoluble. In the presence of the molecular target, the bead attached to one probe further binds with one portions of the target. The other probe attached on the solid surface binds with the other portions of the target. In this way, the molecular target is sandwiched between the functionalized bead and the functionalized solid surface.

In accordance with one embodiment of the present invention, the method of detecting a molecular target in a sample suspected of containing the molecular target, comprises:

attaching to a bead a first molecular probe capable of attaching to one part of the molecular target to form bead-bound probes;

attaching to a support a second molecular probe capable of attaching to a second part of the molecular target to form support-bound probes;

introducing the sample to the bead-bound probes and the support-bound probes and allowing binding of the molecular target to said bead-bound probes and said support-bound probes so that the molecular target is sandwiched between the support and the beads, and the beads are attached on the support;

detecting the presence of beads on the support, wherein the detection of the beads on the support indicates the presence of the molecular target in the sample.

In accordance with the present invention, beads can be detected optically by its effects on light. When a beam of laser light strikes a reflective surface such as the support, it is wholly reflected back and the reflected laser can be detected by a sensor suitably positioned along the anticipated path of the reflected light. In the presence of obscuring material, such as an aggregate of dark, non-reflective beads, only a small amount of laser light is reflected back—the reflected laser light is attenuated owing to scattering of the light in different directions. The opposite effect can be similarly exploited for detection of the beads such that in the presence of reflective beads on a non-reflective surface, reflection of light owing to scattering of some of the light to the sensor occurs. Thus, the presence or absence of beads on a surface can be interrogated by shining a beam of laser light onto the surface and looking for change in the intensity of the reflected laser light. In this way, a binary 0 output signal is modified to a binary 1 signal in the presence of beads, and vice versa. To make it easier to detect the beads, the beads may be aggregated before the detection. After the interaction of the molecular target and the probes, unbound beads and other reagents and sample can then be removed to eliminate noise.

This invention further provides an apparatus for detecting or identifying trace quantities of a molecular target by exploiting the specific interactions between the molecular target and a pair of molecular probes, one of the pair of molecular probes is attached to a bead. The apparatus comprises:

bead-bound probes comprising beads attached to a first molecular probe capable of attaching to one part of the molecular target;

a support-bound probe comprising a support attached to a second molecular probe capable of attaching to a second part of the molecular target;

a means for introducing the sample to the bead-bound probes and the support-bound probes and allowing binding of the molecular target to said bead-bound probes and said support-bound probes so that the molecular target is sandwiched between the support and the beads, and the beads are attached on the support; and a means for detecting the presence of the beads on the support, wherein the detection of the beads on the support indicates the presence of the molecular target in the sample.

A preferred embodiment for this apparatus is to set a microarray of the biochips in this invention along the track of a miniaturized conventional optical disk, with information of the whereabouts and contents of the biochips burned onto the surface of the optical disk by conventional technology.

The conventional optical disc stores binary data by a series of embedded reflective and non-reflective elements along a continuous spiral track starting from the center of the disc. As the disc spins along its central axis, a beam of laser light focused on the track is reflected or scattered as the laser scans the embedded elements. A suitably positioned photodiode receives the reflected laser light or its attenuated reflection, thus reading the binary data on the disc. Burning a conventional optical disk generally involves changing the reflectivity of an embedded medium using thermal energy imparted by a different much stronger laser than the reading laser.

In accordance with the present invention, the apparatus may have a plurality of wells bound with different probes for detecting or identifying different molecules. To quantify different amounts of the same molecule, the apparatus may have a plurality of said wells bound with different amounts of the same kind of probes. For quality assurances, the apparatus may have at least two wells with the same amount of the same type of bound probes for quality control, for example duplications or multiples of the same biochip can be made on the same support. This measure further enables the statistical calculation of a "confidence level" when multiple identical biochips are compared in multiple readings to compensate for manufacturing defects, contaminating dusts and other unforeseen technical glitches. To further make the detection easier, the apparatus may further have means for aggregating the beads bound on the support. For example, an article producing magnetic field can magnetize unmagnetized ferromagnetic beads and cause them to aggregate together.

This invention further provides some methods of increasing the number of bound beads on the biochip surface to provide for another layer of signal amplification in the event of very few target molecules. These methods include the novel method of Magnetic Chain Reaction and other possible methods such as the aggregation of gold nanoparticles functionalized with oligonucleotide probes by the addition of linking DNA duplex (document—U.S. Pat. No. 6,261, 944), the aggregation of biotinylated beads by the addition of avidin or streptavidin or vice versa, the aggregation of beads with attached Staphylococcal protein A or Streptococcal protein G by the addition of immunoglobulin dimers or multimers, the aggregation of biotinylated beads by multivalent anti-biotin antibodies, as well as other methods adapted from immunoassay methods. Thus, one molecule of streptavidin has four binding sites for biotin. The addition of streptavidin to a suspension or solution of beads with attached biotin on the surface causes cross-links between beads, leading to aggregation. In the same way, multivalent immunoglobulin molecules can link beads as they bind to specific molecules (e.g. biotin) on the bead surface, causing the beads to aggregate.

Magnetic Chain Reaction is the phenomenon of spontaneous aggregation of magnets under the influence of their magnetic fields. In this invention, if unmagnetized ferromagnetic material is used to construct the beads, then magnetization of the beads will result in spontaneous aggregation of the beads. This process may or may not require perturbation to assist the precipitation of solubilized beads. For non-solubilized beads, gentle agitation alone may be sufficient to cause the beads to aggregate. Once beads aggregate under the influence of magnetism, detecting them becomes easier.

According to this invention, the presence of beads on the solid surface is detectable by various methods utilizing the physical properties of the beads. Accordingly, if the beads are metallic, a detectable magnetic field can be induced in them by an external magnetic field (metal detection). If the beads are made of ferromagnetic material, they can be detected by first magnetizing them and then detecting the magnetic field of the beads. Ferromagnetic beads can also be heated up by applying a rapidly alternating external magnetic field without heating up non-ferromagnetic metallic and non-metallic components of the machinery. Beads thus heated up emit increased infrared radiation that can then be detected either directly by a sensitive infrared sensor or by any of the following means:

1. Enhancement of chemiluminescence or bioluminescence. Chemical reactions are speeded up by increase in temperature. Enzymatic reactions are also speeded up by thermal energy up to a certain temperature above which the enzyme denatures. Chemical reactions that result in release of light, such as chemiluminescence and bioluminescence reactions can be speeded up by increasing the temperature, thereby resulting in an increase in intensity of light output. This increase in light output can be detected by photodiodes.

2. If the beads are coated with thermoluminescent materials, then heating the beads will result in emission of light that can be detected.

3. The emitted light from the above reactions can be used to "pump" a laser, thereby generating a larger, more readily detectable optical signal by way of light amplification.

The presence of ferromagnetic beads on the biochip surface can also be detected by first magnetizing them and then listening to them by sensitive acoustical instruments while flipping them back and forth by an alternating external magnetic field. This is analogous to the Barkhausen effect, except that the aggregate of beads are separate magnets rather than one magnet.

Various applications of the methods in detecting or identifying any molecular target in the present invention are provided. These applications include but are not limited to the assaying of the concentration of molecules, genetic applications such as mutation detection, single nucleotide polymorphism (SNP) profiling, the counting of repetitive nucleic acid sequences and its uses thereof, the molecular classification and diagnosis of cancer, gene expression analysis, proteomics and drug screening.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

Preferred forms of the present invention will now be described, accompanied by examples, with reference to the accompanying drawings, wherein:

FIG. 6 represents conceptually, a scheme for addressing the biochips and placement of digital landmarks.

FIG. 16 schematically depicts the study of which protein interacts with which using a microarray of proteins and a library of beads, each of which has a different attached protein.

DETAILED DESCRIPTION OF THE PRESENTLY PREFERRED EMBODIMENTS

Definition

Figure 1:
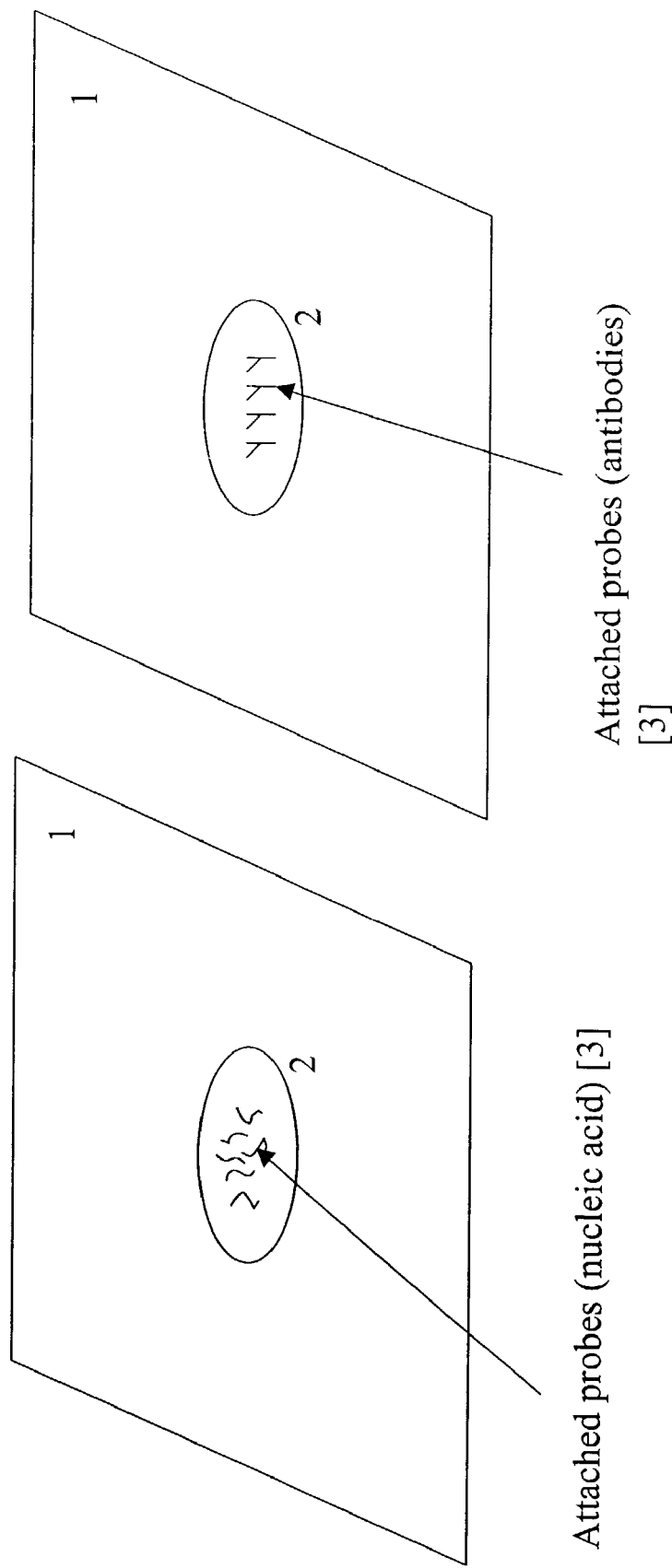
FIG. 1 is a schematic diagram of two biochips, functionalized by binding a probe specific to the target (nucleic acid on left and antibodies on right) to the reaction well.

As used herein, the following terms are intended to have the following general meanings:

"Nucleic acid" means DNA, RNA, single-stranded or double-stranded and any chemical modifications thereof. Modifications include, but are not limited to, those which provide other chemical groups.

"Ligand" refers to a molecule that binds to a receptor specifically and thereby induce a signal in the cell, e.g. a hormone is a ligand which when bound to a receptor triggers a cascade of cellular response leading to growth of the cell or other responses.

"Hybridization" used in this document means fusion of two single complementary DNA strands (DNA/DNA hybridization), or the fusion of complementary DNA and RNA strands (DNA/RNA hybridization).

"Analyte" refers to a substance present in the blood or body fluids of a patient. The concentration of an analyte typically varies with metabolic or pathologic states and is of information to clinicians managing a given patient's health.

"Antigen" means a substance with a molecular surface structure that triggers an immune response, i.e., the production of antibodies, and/or that reacts with (its) specific antibodies (antigen-antibody reaction).

"Antibody" is a protein (immunoglobulin) that recognizes and binds to an antigen as part of the immune response.

"Molecular probe" means any molecules of nucleic acids, proteins or other molecules that have the property of specifically binding to another molecule of the same or a different class. Generally, nucleic acids bind specifically to nuclei acid showing sequence complementarities. Thus, a probe (in this case a nucleic acid molecule) with the following sequence of A-G-G-C-G-T-A (from 5' to 3' end) will bind specifically with another strand of DNA containing a region with the following sequence of T-A-C-G-C-C-T (from 5' to 3' end), where A, T, G and C stand for adenine, thymine, guanine and cytosine, respectively. An antibody to an antigen can be used as a molecular probe against that antigen.

"Epitope" refers to the part of an antigen molecule that binds to an antibody. An antigen can have many different epitopes, which bind to different antibodies. "Ferromagnetic beads" refers to beads composed of any substance with inducible magnetic property that generates heat in the presence of a rapidly alternating magnetic field owing to induction of eddy currents within the ferromagnetic beads.

"Microsatellite" refers to small run (usually less than 0.1 kb) of tandem repeats of a very simple DNA sequence, usually 1–4 bp, for example (CA)n.

"Microsatellite instability" refers to a phenomenon characteristic of certain tumor cells, where during DNA replication the repeat copy number of microsatellites is subject to random changes.

"Polymerase chain reaction (PCR)" refers to a technique for making many copies of a stretch of DNA sequence in the test tube. It employs repetitive thermal cycling consisting of denaturation of double-stranded DNA, annealing of appropriate oligonucleotide primers, and extension of the primer by polymerase enzyme.

"Reverse transcriptase" refers to an enzyme complex that occurs in RNA viruses and that can synthesize DNA from an RNA template.

"Reverse-transcription PCR (RT-PCR)" refers to the technique for amplification of RNA involving first the synthesis of DNA complementary (cDNA) to a stretch of target RNA employing the enzyme reverse transcriptase, followed by PCR of the cDNA.

Architecture of the Biochip

The biochip consists of a small spot (well) on a solid support made of any kind of material, but preferably a stiff, transparent polycarbonate polymer coated with reflective inert material such as gold. On the biochip surface is bound one of a pair of molecular probes that is specific for the putative target.

FIG. 1 is a schematic representation of the biochip [1], comprising a solid support with a central "well" [2] to which are covalently bound nucleic acid probes [3] (left), specific antibodies [3] (right), or other molecules.

The other component is a second specific probe that is bound to small dark, non-reflective solubilized or non-solubilized (bottom-dwelling) beads of, electrically conductive, semi-conductive or non-conductive material, preferably ferromagnetic, such as iron, iron oxide, singly, electroplated, or in various combinations or alloys.

Principles of the Biochip

Figure 2:
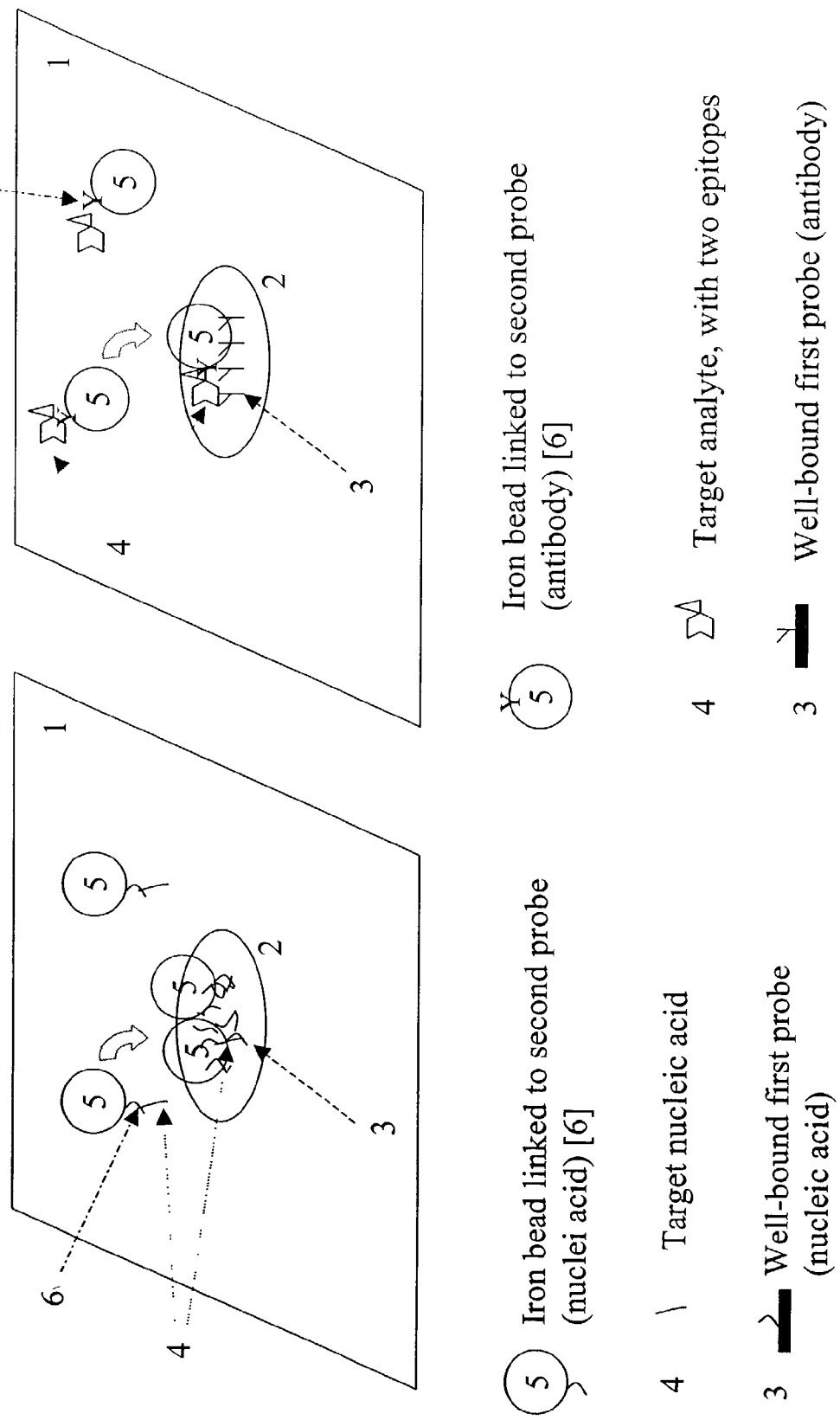
FIG. 2 shows schematic representations of two biochips with attached beads, bound to the biochip because of specific binding between functionalized biochip, target and functionalized beads (having attached probes specific for a different region of the target), FIG. 3 schematically depicts the addition of a ligation step in biochips with nucleic acid probes.
Figure 4A:
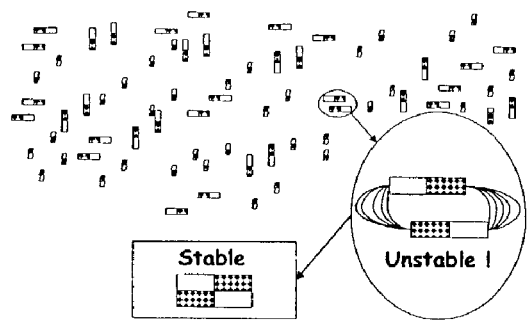
FIG. 4 depicts Magnetic Chain Reaction and the amplifying effect it has on the number of beads bound to a biochip.
Figure 4B:
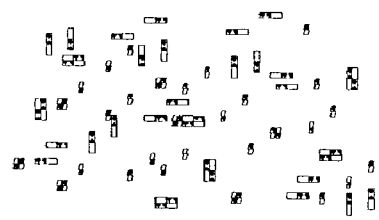
Figure 4C:
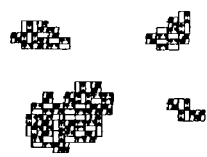
Figure 4D:

Employing the architecture of this biochip and specific probe bound-biochip and beads, when a target is present and under the right conditions, it is bound to and sandwiched between the two probes. FIG. 2 illustrates the concept. Here, some target molecules [4] are captured by beads [5] functionalized by specific probes [6] and well-bound probes [3]. Others target molecules are bound to functionalized beads or wells but not both. By virtue of the location of the well-bound probe [3], functionalized beads [5] bound to target molecules [4] are fixed to the well [2] of the biochip [1]. Nucleic acid probes and targets are depicted on the left and specific antibody probes and antigenic targets are depicted on the right. After the reaction, unbound beads and other reagents and sample can then be removed to eliminate noise and the beads detected by various means.

The detectable range of concentration of the target is extremely wide, from one single molecule to as many as there are bead bound-probes, providing for robustness of design. Yet, the sensitivity is not compromised. This setup can theoretically detect the presence of only one target molecule. In addition, when used for the detection of specific nucleic acid sequences, no prior amplification is necessary. This method is versatile and can be used to detect DNA, RNA, proteins, and other macromolecules.

Creation of Molecular Probes

A pair of specific molecular probes is first created.

Nucleic acid probes can be constructed with knowledge of the sequence of the target. Such sequence information can often be found in databases such as Entrez-Genome (National Center for Biotechnology Information, National Library of Medicine, National Institutes of Health, USA). Probes with sequences complementary to the two ends of the target can be synthesized commercially. In addition, probes can be designed in such a way that upon hybridization with the target, the two ends of the probes are brought into physical proximity such that a DNA-ligase (an enzyme that covalently joins DNA strands that are brought together) can ligate the two ends to strengthen the bond between beads and "well". Antibodies can be produced from laboratory animals exposed to the antigen. Because of that, a source of antigen is required.

The Reaction

The adequately prepared sample is added to the chip. Air containing a putative target can be bubbled through a suitable solute. Solid or liquid can be dissolved in solution. Intact cells and tissue may be required to be lysed chemically or physically or otherwise prepared to liberate the molecule being detected.

Functionalized beads are added in excess of the target (prior to, during, or after the addition of the sample). If the target is double-stranded DNA, a predetermined period of heating at a specific temperature may be required to denature the DNA into single stranded DNA. Reaction is allowed to happen.

A solution to microfluidic challenges is explained in this preferred embodiment, where beads are made of demagnetized magnetic material and held stationary on a spot on the surface of a spinning microarray of biochips by a movable magnet under the microarray so as to systematically and sequentially interrogate the passing biochips for captured targets. This alters the kinetics of the reaction in a favorable direction since the stationary beads move against the target in solution and the passing biochips. The magnetic field that holds the beads should not be so strong as to permanently magnetize the beads at this stage.

To enhance the specificity of the hybridization reaction between nucleic acid target and nucleic acid probes, an optional step of ligation of the two probes may be included. This is illustrated in FIG. 3. The oligonucleotide probes [3 & 6] are designed to hybridize to an adjacent stretch of target sequence [4] in such a way that the ends meet. Addition of DNA ligase [7] results in covalent linkage of the sugar-phosphate backbone of the oligonucleotide probes. In addition to enhancing the specificity of the reaction, this step also strengthens the linkage of the bead to the biochip so that the beads or beads aggregated around the specifically bound bead(s) (next section—Aggregation of Beads) tethered to the biochip by a single molecule of nucleic acid will not break from hydraulic pressure imposed during washing or mild centrifugal forces on spinning of the biochip microarray.

Aggregation of Beads

In a preferred embodiment, agglutination of the beads is brought about by adding to the biochip, at the end of the reaction, molecules that bind with high affinity and specificity to chemical moieties on the beads. Such chemical interactions include but are not limited to:

1. Avidin/biotin or streptavidin/biotin—Avidin and streptavidin each have four binding sites for biotin. Thus beads with biotin bound on the surface (biotinylated) will aggregate when avidin or streptavidin is added to a suspension (or solution) of such beads because the avidin (or streptavidin) links two or more beads together and other biotin molecules on the bead surface are free to link up with more avidin (or streptavidin) molecules and hence other beads.

2. Protein A/IgG or protein G/IgG—Staphylococcal protein A and Streptococcal protein G have strong affinity for the Fc (crystallizable fragment) of the immunoglobulin molecule. Since each immunoglobulin G (IgG) molecule has only one Fc fragment, it takes immunoglobulin dimers, such as two molecules of IgG bound to a common antigen with two or more identical epitopes to cause cross-linking of beads containing protein A or protein G on the surface.

3. Antibody/antigen pairs—anti-biotin antibody raised against biotin can cause aggregation of beads with biotin molecules bound to the surface. Polyvalent antibodies, such as IgA and IgM are more effective in causing aggregation of beads because they are divalent and pentavalent, respectively.

4. DNA/DNA, DNA/RNA—suitably engineered beads with attached nucleic acid molecules can be caused to aggregate when linking duplex DNA with complementary sequence is added (Mirkin, document U.S. Pat. No. 6,261, 944).

5. Other specific molecular interactions that can be exploited. For example, enzymes bind to substrates to catalyze reactions. If instead of the natural substrate, a small molecule (such as a drug) with similar configuration but is not cleaved by the enzyme is added to the solution, it will bind with avidity to the enzyme. A small molecule with more than two enzymatic binding sites can cause aggregation of beads if the enzyme is bound to the bead surface. Gp120, a protein produced by the HIV virus binds specifically to the CD4 molecule produced by the human T-cell. Thus beads containing gp120 can be agglutinated if T-cells are added to the solution.

Magnetic Chain Reaction for Aggregation of Beads

In a particularly preferred embodiment, herein referred to as the Magnetic Chain Reaction, ferromagnetic material is employed for the beads. The beads are initially demagnetized. After completion of the reaction with the target, the biochip or the entire microarray of biochips are subjected to a sufficiently strong magnetic field to magnetize the beads. The beads are previously solubilized, suspended or otherwise dwelling at the bottom of the biochip and not interacting with each other. After the transfer of the energy of magnetization to the beads, they begin to interact with each other because of the presence of net magnetic field owing to the remanence of the material. The system of beads will interact in such a way as to seek the lowest possible energy state. This lowest energy state is the alignment and aggregation of the beads. Because the unbound beads aggregate into one big clump, the reaction is dubbed "Magnetic Chain Reaction". The aggregates attach to the also magnetized beads that are specifically bound to the biochip and not to biochips that do not carry bound beads. Magnetization of ferromagnetic beads is readily achieved by the application of a magnetic field generated by an electromagnet, such as is found in the consumer-type tape recorder.

Whereas individual bound beads on a biochip are difficult to detect, a large aggregate is easy to detect and may even be visible to the naked eye, making it possible to employ various methods to detect the aggregates.

FIG. 4 schematically depicts the stages that follow magnetization of the beads, leading to the formation of aggregates of ferromagnetic beads. This is dubbed magnetic chain reaction.

Methods of Detection of Beads

1. Detection of beads by scattering of laser light

In a particularly preferred embodiment, attenuation of reflected laser in the presence of bound beads is used as a means of detection of specific reaction of target with well-bound and bead-bound probes.

If the biochips are supported on a reflective medium, then laser light focused on a biochip without bound beads will be reflected back. A strategically positioned photodiode (sensor) detects the reflected laser.

Biochips that are covered by aggregated beads scatter the laser; as a result, laser of diminished intensity is reflected back to the sensor.

In this way, specific reactions on the biochip can be readily detected and binary signals generated.

Figure 5A:
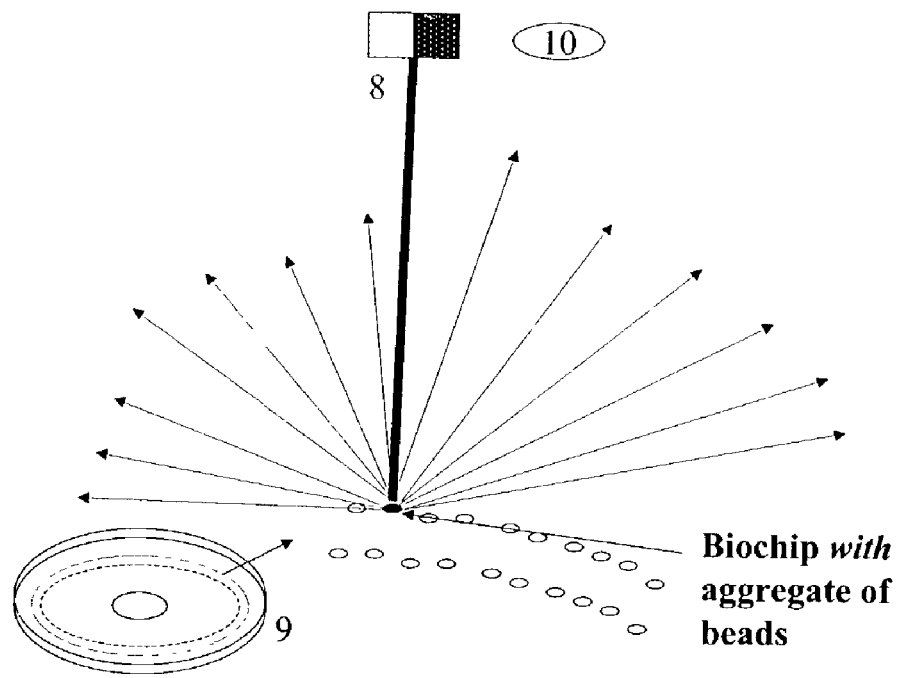
FIG. 5 is a schematic representation of a spiral-linear microarray of biochips and the preferred scheme to detect the presence of aggregated non-reflective beads on the biochip by scattering of laser light in their presence and the reflection in their absence. The supporting medium must be reflective to laser light.
Figure 5B:
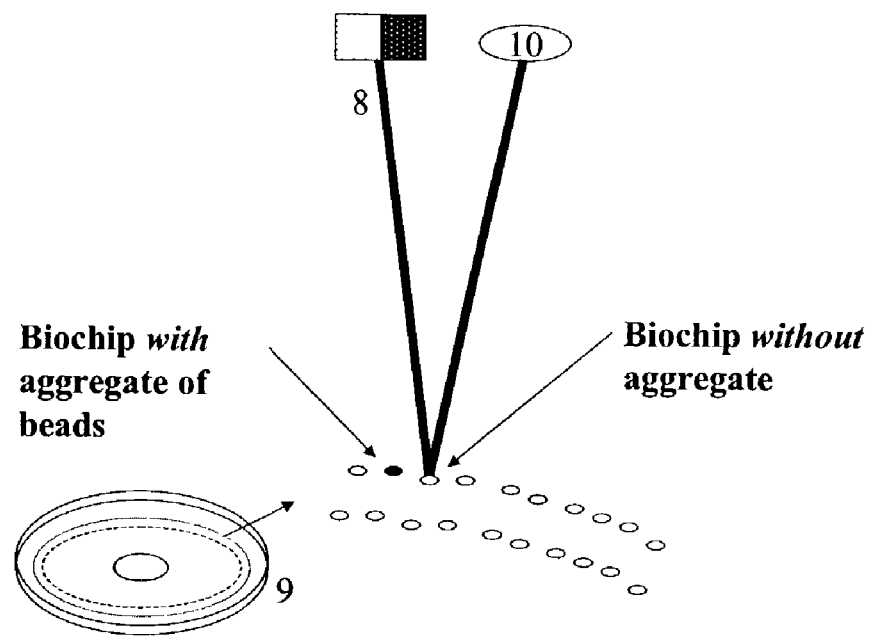

FIG. 5A shows the scattering of a scanning laser beam [8] in the presence of an aggregate of non-reflective beads on the biochip [1]. The biochips [1] are depicted as aligned along a spiral track on a diminutive compact disk-like microarray [9], superimposed on the track and fully integrated with the reflective and non-reflective (digital) elements of the track. For clarity, only the middle two spirals are shown. In the absence of an aggregate of beads (FIG. 5B) and if the biochip is made of reflective material, the laser beam will be reflected back to the sensor [10]. This BINARY signal (presence (1) or absence (0) of beads) is relayed to a built-in microprocessor, which together with information on what is present on the biochip, provides the result of the analysis. Rather than a single spiral track, multiple concentric tracks or some other formats may be used.

Alternatively, beads can be made of reflective material and the biochips are located on non-reflective elements of the track. Binding of beads on the biochip surface achieves the same objective of modifying the encoded signal from non-reflective (binary 1) to reflective (binary 0).

In another embodiment, the microarray takes advantage of both surfaces of the disc (transparent microarray), with digital information (reflective or non-reflective) encoded in a layer embedded within a transparent supporting medium. The biochips are on the upper surface of the disc. Using a laser under the disc and two sensors, one on each side of the disc, the sensor on the same side (tracking sensor) as the laser functions as the reader of the encoded digital information as in a conventional optical disc, whereas the laser on the opposite side (biochip sensor) functions as detector for the presence of beads that in their presence would attenuate the laser transmitted to the biochip sensor. The tracking sensor is gated to ignore the faint back-scattered laser from the undersurface of the biochip in the event that beads are bound to the biochip surface. Similarly, the biochip sensor is programmed to ignore signals other than those coming from biochips.

In yet another embodiment, the same transparent microarray is employed. Digital information is encoded as opaque and transparent bits. The interrogating laser is positioned on the opposite side of (under) the biochip and a single detector on the same side as the biochip functions as both tracking and biochip sensor. This embodiment detects the attenuation of the transmitted laser by the beads in locations otherwise transparent to laser. In this embodiment, biochips are located on transparent bits.

FIG. 6 depicts a scheme of integrating the biochips with digital encoding and the use of error-correcting EFM (eight-fourteen modulation), so as to provide feedback to the microprocessor as to which part of the microarray the laser is scanning, the address of the biochips and the contents of the biochips. In FIG. 6A and FIG. 6B, the three rows read as one continuous string, with no spaces between (spaces are depicted for clarity). Each block of 14 binary digits encode a keyboard stroke (here represented arbitrarily). At the appropriate location, the medium is converted to a biochip by the deposition of probes. Here the anthrax biochips [11] are indicated and carry oligonucleotide probes against anthrax lethal factor. In the presence of DNA sequences encoding anthrax lethal factor extracted from specimen anthrax spores, these will be bound to the biochip as well as to functionalized beads carrying oligonucleotide probes specific to a different region of the anthrax lethal factor. The presence of attached beads on the biochip is detected by laser scanning, with or without Magnetic Chain Reaction. In this illustration (FIG. 6A), when the biochips contain laser scattering beads, the block (11011011010100) reads as 'Y' for beads present, whereas in the absence of beads, the block (11001011000100) reads as 'N' for beads not present. In FIG. 6B, the concept of "degeneracy" of coding is illustrated, with 10011011010100 and 10111011111100 both indicating positive identification of anthrax. Because large aggregates may spill over the biochip boundaries into adjacent domains (each '0' or '1' is a digital domain), different codes are made to code for the same result. This "degeneracy" of coding mimics Nature's coding of amino acids by multiple codons. For example, CCA, CCG, CCC and CCU all encode the amino acid proline.

2. Metal Detection.

This is applicable to beads that are metallic or have substantial amounts of metal. The principles of metal detection have been described elsewhere. Briefly, a metallic object produces internal eddy currents that result in an opposing magnetic field when perturbed by an external magnetic field. The induced magnetic field is in turn detectable by sensitive electromagnets.

3. Detection of Magnetic Field after Magnetization.

Using a sensitive gaussmeter or other devices, the magnetic field of the aggregated beads can be detected. Indeed, the detection of the magnetic field of tiny magnets on ordinary magnetic tape, digital tape and computer hard disks is exploited as a means of storage and retrieval of analog and digital data.

4. Detection of Sound.

Barkhausen effect describes the crackling noise emitted from permanent magnets upon perturbation by a fluctuating magnetic field. This noise is attributed to the interactions between adjacent magnetic domains in the magnet caused by forcible alignment imposed by the external magnetic field.

The Barkhausen effect can be exploited in the detection of aggregates of magnetic particles.

5. Detection of Heat/Infrared Emission Emanating from Beads after Excitation by External Field (Energy Source) Such as Alternating Magnetic Field and Electromagnetic Wave.

In the presence of an externally applied electromagnetic field, metallic particles absorb energy, causing the particles to heat up. The heat is in turn radiated as infrared rays.

a. Infrared emission can be detected by a sensitive infrared photodiode alone or in combination with a laser beam (laser thermometer).

b. The heat emitted to the immediate environment of the beads enhances the chemiluminescence of the surrounding chemiluminescent mix, if such is previously included in the biochip by virtue of the speeding up of chemical reaction due to heat. The light generated by the chemiluminescence is of sufficient intensity to be detected by a photodiode and is proportional to the amount of bound beads, the degree to which they are excited by the external field and the duration of application of the external field.

c. Enhancement of bioluminescence of surrounding bioluminescent mix occurs by the same principle. Again, the light emitted can be used to detect and quantify the beads.

d. Induction of luminescence of thermoluminescent material previously coated on beads. Thermoluminescent material radiates excess thermal energy as visible light. The light emitted can be detected by photodiode.

e. In-situ light amplification of built-in laser by light emitted from a–d. By building in a small laser, the light emitted from the beads or their immediate surroundings can be used to "pump" the laser to generate a laser beam by the principle of Light Amplification by Stimulation of Emission Radiation. The laser so generated can be used to signal the presence of a specific reaction at the biochip, thereby identifying the presence of the target molecule being detected. A photomultiplier tube achieves the same end.

Fabrication of a Microarray and Point-of-Care Device

Figure 7:
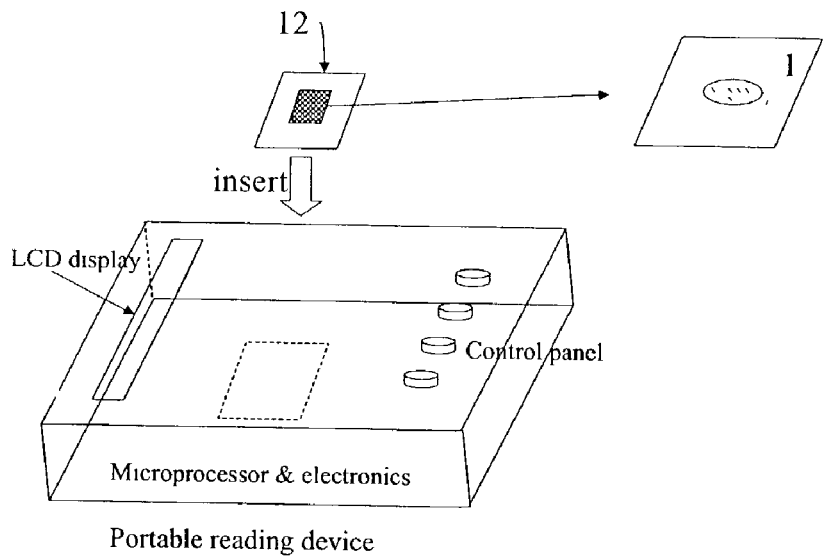
FIG. 7 depicts a design of a portable device for use at the point-of-care.

In a preferred embodiment, multiple single chips are fabricated into a two or three-dimensional grid-like microarray. In FIG. 7, the schematic drawing of such a microarray [12] is depicted, fitting into a portable device for point-of-care. The laser scanner and other electronic components are omitted for clarity. The individual biochips can be made to detect different molecules or perform different quantitative analyses. Duplications or triplications of the same chip can be made on the same microarray for quality assurance purposes.

In a particularly preferred embodiment, a spiral linear microarray of biochips are intercalated with digital landmarks in the form of "land" and "pit" on a circular reflective surface as in an optical disk.

The "land" and "pit" scatter or reflect, respectively, a beam of tightly focused laser light, which is then interpreted by the sensor as corresponding to binary "ON" or "OFF"; thus encoding information about where the laser beam is scanning as well as information about the biochips.

Scanning the biochip by the laser reveals the presence or absence of particulate aggregate, the presence or absence of which would correspond to the "land" and "pit", respectively of the digital landmarks intercalated between the biochips.

Figure 8:
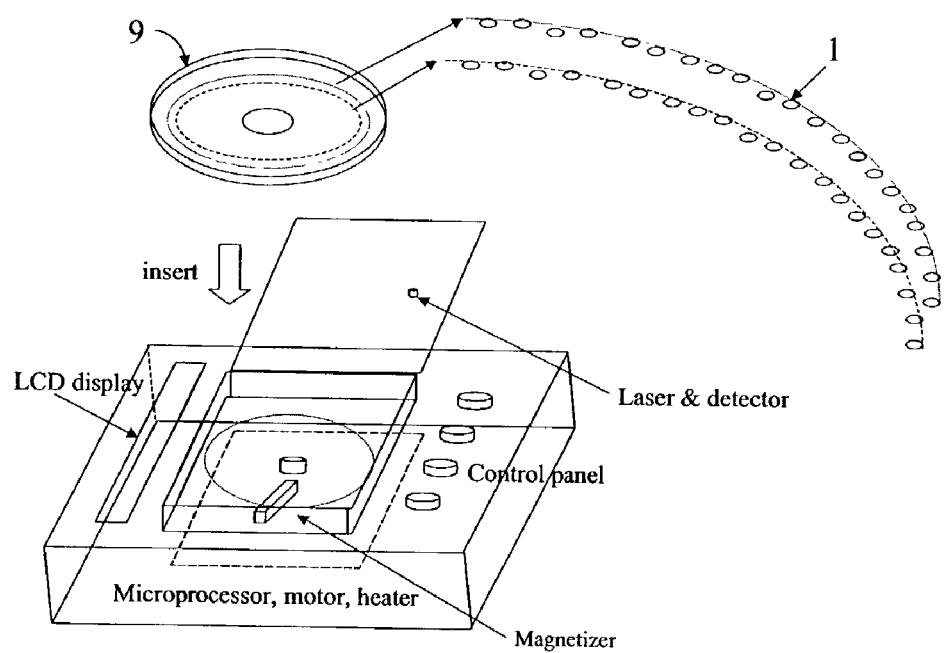
FIG. 8 depicts a preferred design of a portable device using the preferred spiral-linear microarray, FIG. 9 schematically depicts the principles behind one method of competitive assay, and how its use in a microarray of many biochips permits the assay of the concentration of an analyte, FIG. 10 schematically depicts the principles behind the second method of competitive assay.

FIG. 8 illustrates the particularly preferred embodiment of microarray, resembling in many ways the optical disk. The microarray is made of plastic and coated with reflective material, is circular or of any shape that spins around a central hub. "Pits" and "land" are burned or printed onto them by conventional compact disk burner technique to provide feedback information for the microprocessor (digital landmarks), biochip addresses and biochip contents (digital barcodes). At pre-programmed locations (biochip addresses), no 'land' is printed. Instead, one of a pair of probes (nucleic acid, antibody, protein, or other macromolecules) is deposited and attached (printed) onto the biochip by a specially adapted arrayer of the inkjet type that is guided by a laser beam. The other of the pair is attached to beads in a separate process. The track on which the digital landmarks and biochips are located is spiral and begins from the center of the microarray as in a regular optical disk.

For use at point of care, a portable device is constructed which has a slot that accepts the cassette. The cassette contains the microarray and confines the reagents and sample to the surface of the microarray. It contains ports for introduction of specimen and reagents, troughs for the collection of unbound beads and reagents by centrifugal force at the end of the reaction and other features as may be deemed appropriate to the efficient functioning of the microarray. The top of the cassette is transparent to permit interrogation of the biochips and digital information on the microarray surface by the laser and sensor. Inserting the cassette places the microarray in alignment with mechanical gears, electromagnet, laser, sensor and other components of the portable device. The sensor identifies the microarray, performs electronic self-check and at the end of the reaction displays the result as "biological agents" detected, the "concentration" of the analyte or the results of other scientific investigations performed by custom microarrays.

Quantification (Molecular Assay)

Known biological molecules in body fluids often need to be assayed for the concentration. An example is the assay of thyroid hormones in thyrotoxic or hypothyroid states. This invention can be adapted to assay in a timely fashion the concentration of various analytes in point-of-care assays by the bedside or in the clinic using a tiny sample of body fluid or blood.

a. Method 1:

Employing previously fixed beads in a series of biochips, each differing in having slightly less bound analyte molecules and hence functionalized beads, the concentration of an analyte in an unknown sample can be determined (FIG. 9A & FIG. 9B). Addition of the test sample [13] results in competitive binding and displacement of bead-bound-probes. Only those biochips with sufficient bound beads will have detectable signal using any of the methods of detecting beads. Biochips from which beads are displaced beyond the threshold of detection will register a negative signal. The transition point between the series of signal-emitting and signal-silent biochips is correlated with the concentration of the analyte. Prior calibration with known standards permits accurate quantification of the test sample.

In FIG. 9A, competitive binding and displacement of previously bound bead and sandwiched analyte by added specimen is depicted. The higher the concentration of the analyte in a given specimen, the more the previously bound beads is displaced.

Figure 10A:
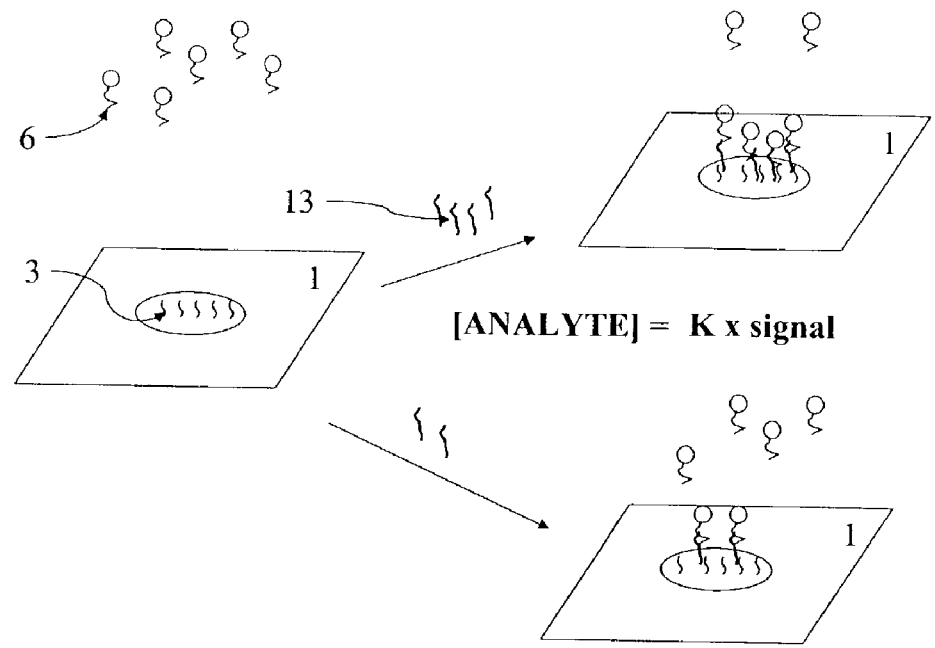
FIG. 10A depicts the scenario of an analyte present in less quantity than the beads and FIG. 10B depicts the scenario of an analyte present in excess of the beads.

FIG. 9B depicts a microarray containing a series of biochips with decreasing amount of bound beads. The addition of a specimen containing the analyte [13] in unknown concentration results in a specific biochip beyond which the beads as detected by laser scattering or the signal emanating from the biochip as induced by an external field is beyond the threshold of detection. The location of this cutoff point gives information on the concentration of the analyte.

b. Method 2:

Another method of quantification of an analyte (FIG. 10A) involving the principle of competitive binding does not require prior fabrication of an array of biochips with fixed beads and analyte. The advantage is that no prior manufacture, isolation and purification of analyte molecule are needed. The prepared undiluted sample (FIG. 10A, upper right) is added to a biochip in parallel with a diluted sample (FIG. 10A, lower right) added to another biochip.

In a preferred embodiment, at least one or two biochips are used. On addition of analyte and functionalized beads to the biochip, binding occurs between the two probes and the analyte, resulting in varying proportion of the following products: analyte bound to functionalized beads, analyte bound to biochip, analyte bound to both biochip and functionalized beads and free analyte.

If the analyte is present in absolute quantity less than the absolute quantity of probes bound to beads, all the analyte molecules are captured by the functionalized beads. Dilution of the specimen will result in lesser quantity of analyte being available for capture and hence the amount of beads that bind to the biochip. The signal strength is directly proportional to the concentration of the analyte when the analyte is present in lesser quantity than functionalized beads with bound probes.

If the analyte is present in absolute quantity more than the probes bound to beads, addition of analyte in excess of functionalized beads results in free analyte in addition to analyte bound to biochips. Because of the limited amount of biochip-bound probes, competition occurs between free analyte and analyte-bound beads. Dilution of the sample and testing in an identical biochip with equal amount of functionalized beads results in fewer free analyte molecules in competition with analyte-bound beads. This accounts for paradoxically larger amount of bound beads and the inverse relationship between the concentration of an analyte and the amount of biochip-bound beads. The signal strength is therefore inversely proportional to the concentration of the analyte when the analyte is present in larger quantity than beads with bound probes.

By running parallel assays on diluted and undiluted sample containing an unknown quantity of an analyte, it is possible to determine the concentration of the analyte by using an equation and a constant value that befits the circumstances as explained above. The algorithm is used by the microprocessor for selecting the appropriate equation for computation of the concentration of the analyte. For most analytes, the range of concentrations frequently falls into either of the above scenarios but not both. Prior calibration and determining the value of the constant is required. Since the method uses only a few biochips for a given analyte, multiple duplications can be built in for quality assurance. Excess capacity can be used in multiplexed assays for many different analytes at once using one microarray in a point-of-care device.

Other Applications

1. Identification of infectious disease agents

Many infectious diseases have similar manifestations. For example, anthrax, influenza, dengue fever, smallpox, simple colds, roseola etc. have initial manifestations that include malaise (poor general well-being), fever, muscle aches and non-specific rashes.

In order that primary care doctors can accurately identify these numerous diseases with similar manifestations but hugely different outcomes, this invention can be adapted to detect minute (hence early) quantities of an entire panel of these infectious agents in the clinic, economically and immediately. Many patients do not even need to be hospitalized for observation and can be sent home with positive identification of the cause, saving both money and risks to the patients (if they need to be warded in a hospital which may harbor harmful microorganisms).

Figure 11A:
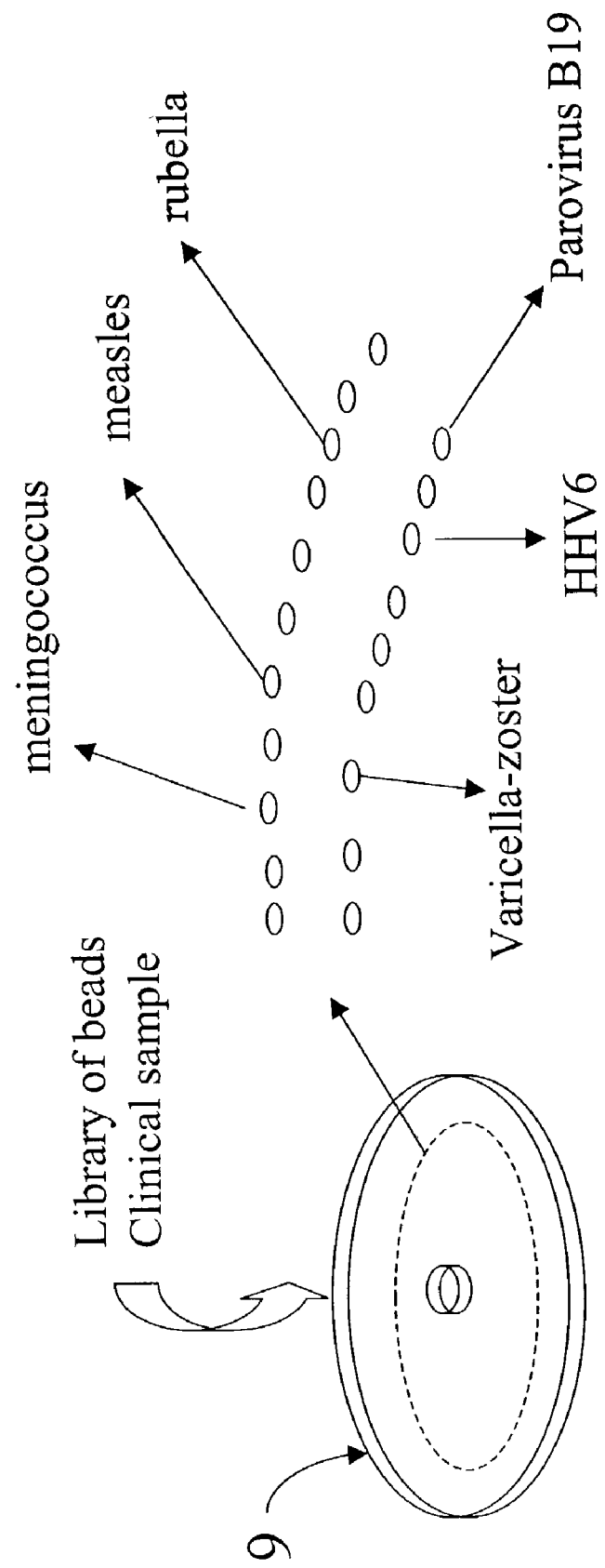
FIG. 11 represents schematically a diagnostic biochip microarray for the adjunctive assessment of childhood exanthematous fevers.
Figure 11B:
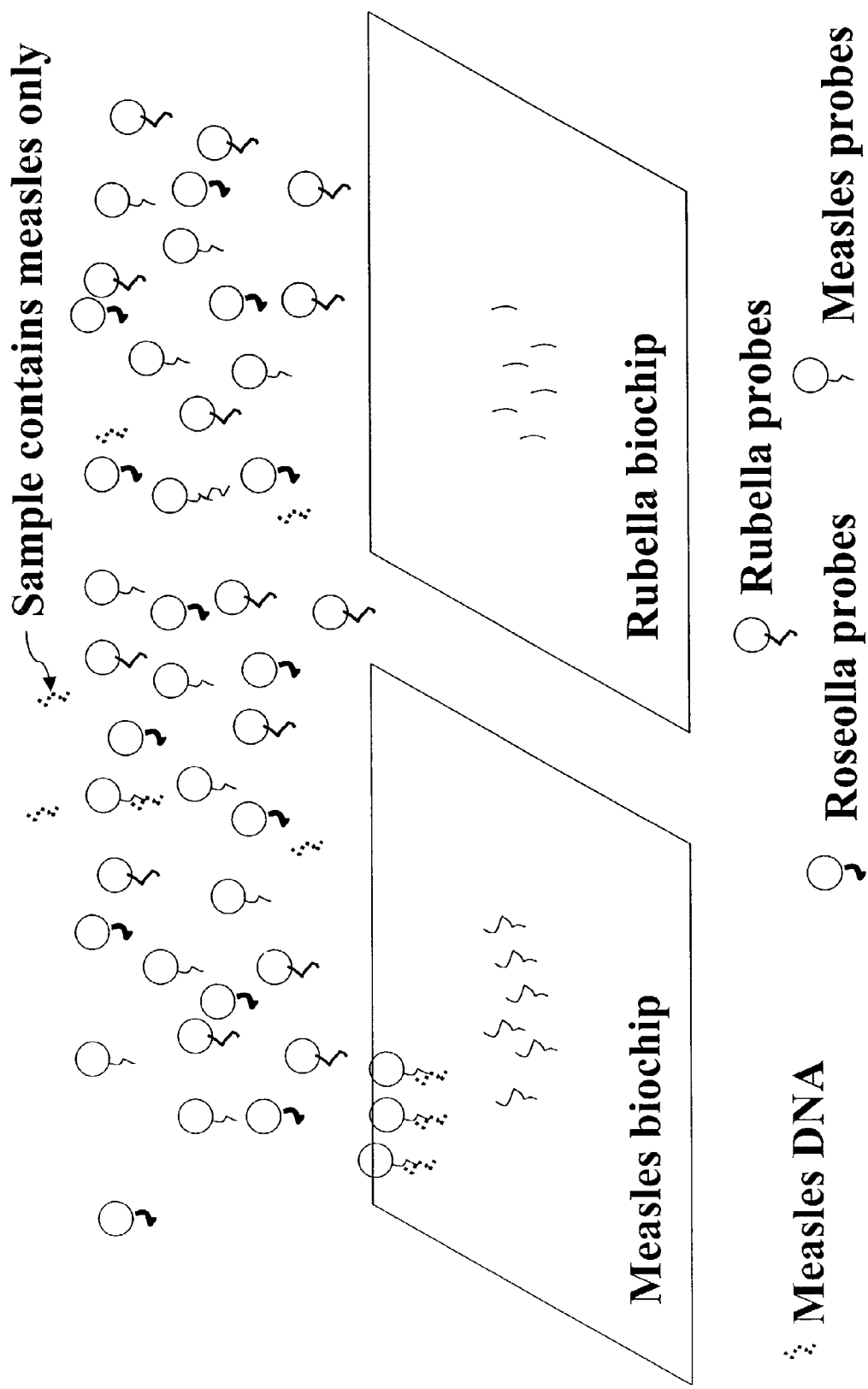
Figure 11C:
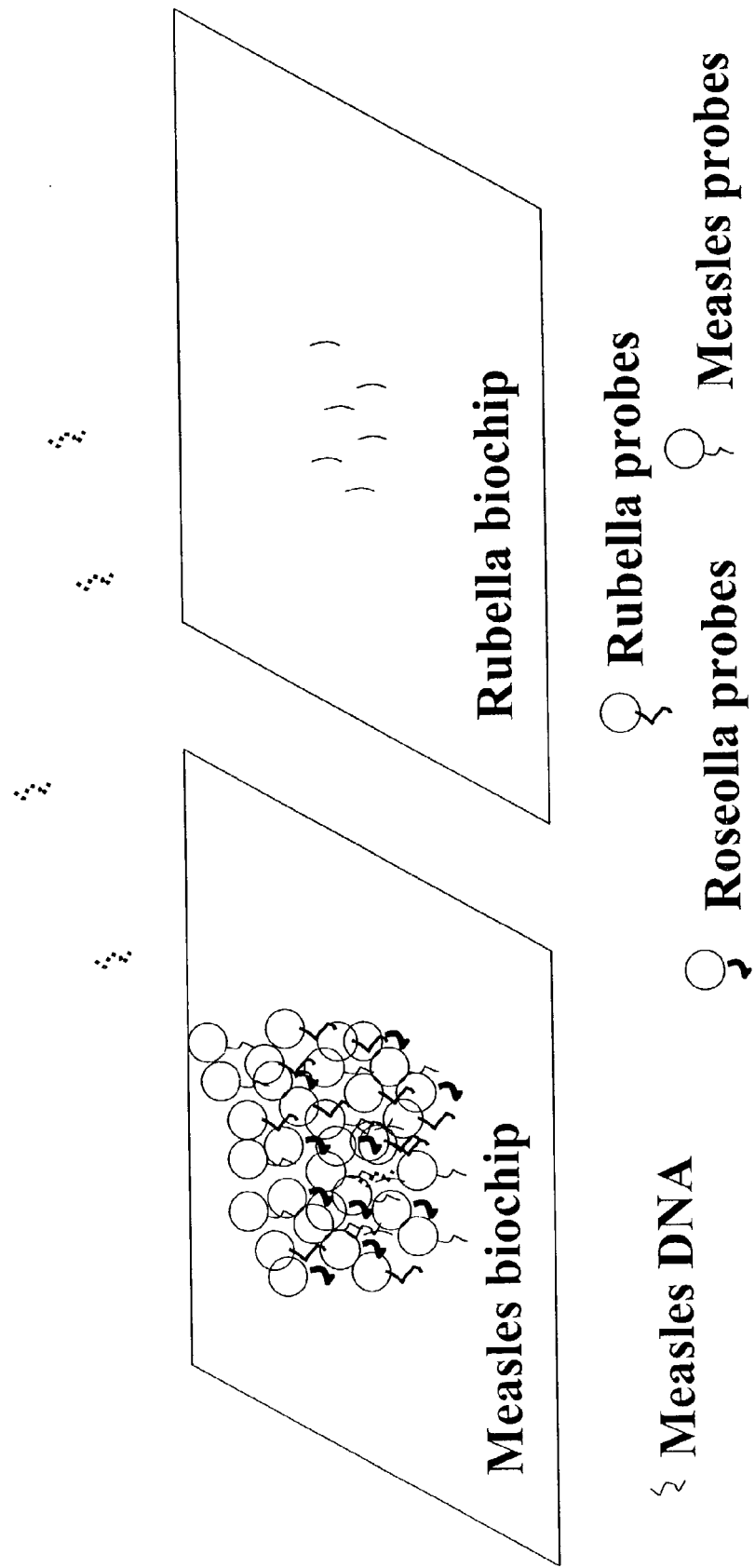

In FIG. 11, the utility of this invention as an adjunct to clinical diagnosis of infectious diseases is illustrated by one possible disease-orientated microarray panel. Depicted here is a microarray that identifies a panel of infectious disease agents with the common initial manifestation of fever and skin rash in children. Although the initial manifestations of these diseases are similar, the evolution, ultimate fate if unaltered and treatment, are considerably different. Thus, whereas roseola infantum infection is mostly inconsequential in immunocompetent children, meningococcal infection has a rapid course and high morbidity and mortality. Using a microarray of biochips [FIG. 11A], to each of which are attached a probe for a different infectious disease agent, the addition of a library of functionalized beads [FIG. 11B] corresponding to the infectious disease agents being sought, and the clinical sample, will result in the attachment of only the type of functionalized beads to the corresponding biochip for the specific type of infectious disease agent. In this hypothetical case, measles is identified by virtue of the binding of functionalized beads to the measles biochip (FIG. 11C, left). No beads are bound to the rubella biochip (FIG. 11C, right), which is read as negative for rubella.

2. Molecular Classification of Tumors

Many cancers are caused by the transposition of a portion of one gene to or within another gene(s) (chimeric genes). Examples are too plenty to list and include follicular carcinoma of thyroid, certain acute myeloid leukemias, many soft tissue sarcomas such as synovial sarcoma and extraskeletal myxoid chondrosarcoma.

Whereas identification of the mRNA transcripts (chimeric transcripts) of these chimeric genes is readily performed by conventional RT-PCR, the method is slow and laborious.

Using this invention (FIG. 12), a pair of probes can be made that hybridize to the two components of the chimeric transcript. One probe is bound to the well and the other is bound to beads. Positive identification can therefore be achieved even with a minute sample harnessed by a fine needle from the tumor or from the blood, if the tumor is leukemia or one that readily enters the blood stream in the early or late course of the disease. Many different cancers can be screened at once in this way.

Figure 12B:
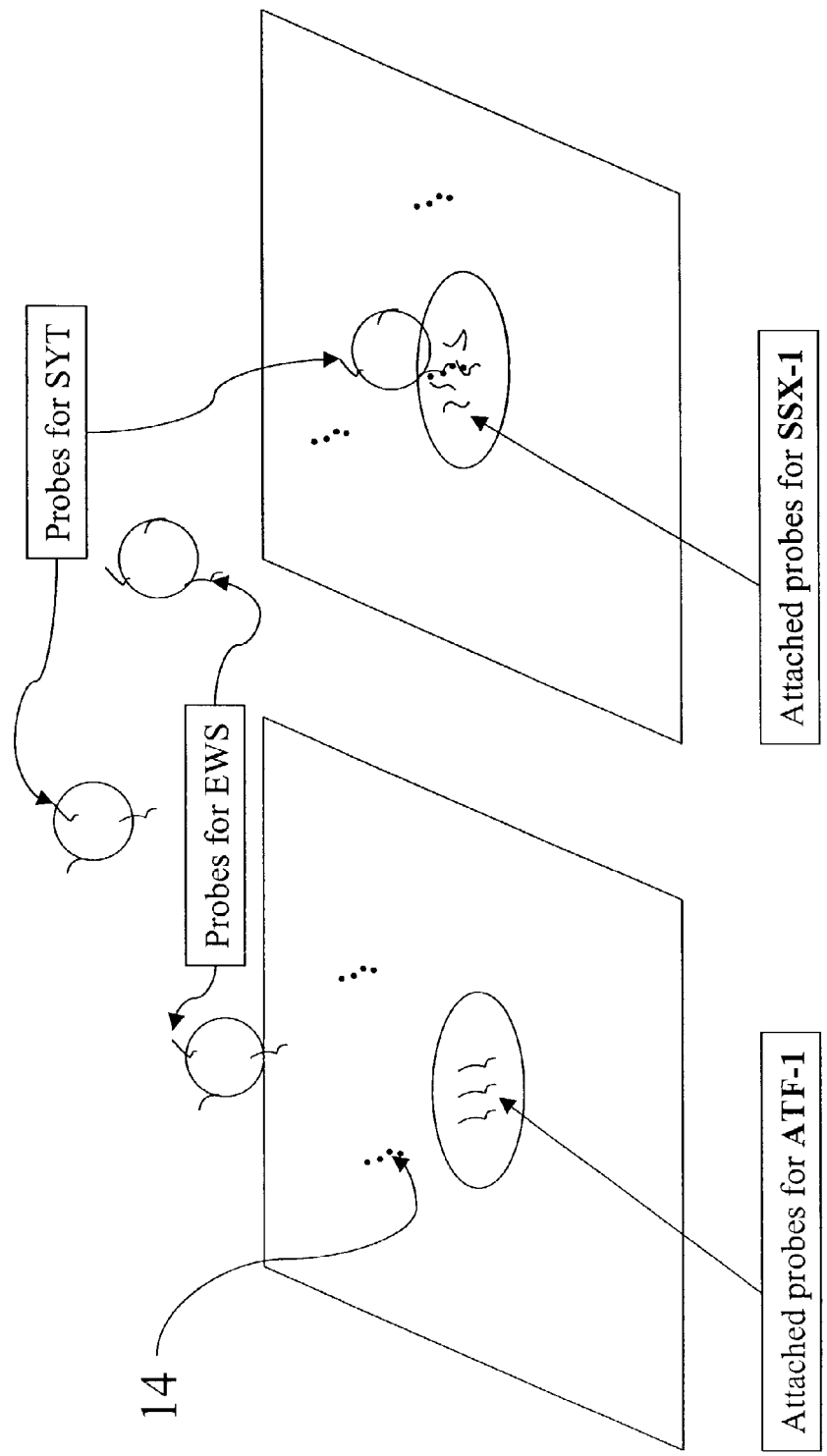
FIG. 12 represents schematically another application of the biochip microarray in the diagnosis and molecular classification of various cancers characterized by genetic translocations, in this illustration, soft tissue sarcomas.
Figure 12C:
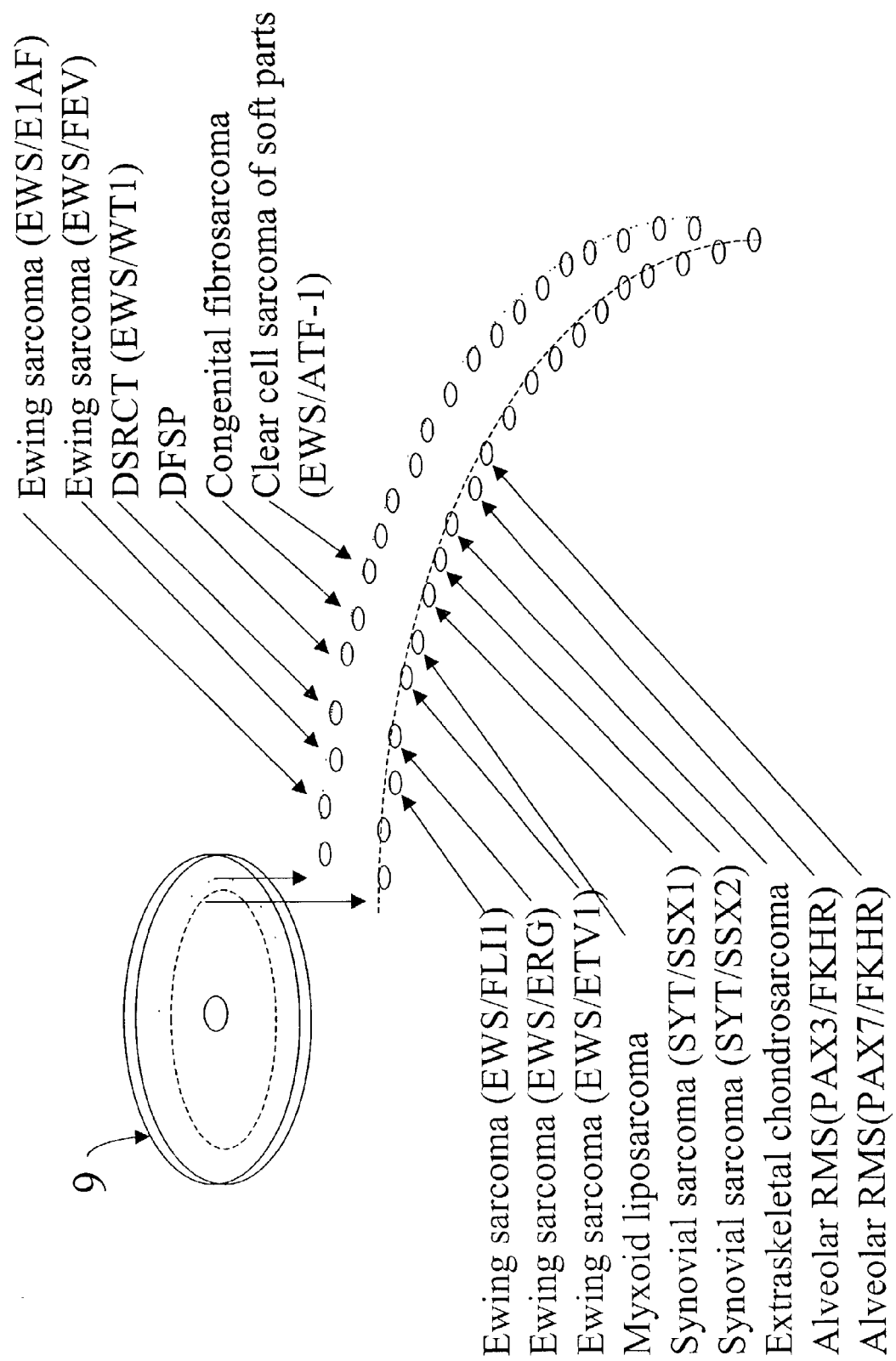

In FIG. 12, this invention is depicted as a molecular diagnostic tool for probing the two or more components of a chimeric stretch of nucleic acid unique to a number of neoplasms, illustrated here, the soft tissue sarcoma synovial sarcoma. Synovial sarcoma is characterized molecularly by the translocation of SYT to SSX1 (or SSX2 or SSX3). Here, tumor cells obtained by fine needle aspiration are suitably prepared and the mRNA [14] loaded onto the biochip microarray. The biochip on the left [FIG. 12A & FIG. 12B] have attached probes specific for a stretch of ATF1 transcript (in this instance, for clear cell sarcoma of soft parts) and the one on the right [FIG. 12A & FIG. 12B] to SSX-1. Other biochips (not shown) on the same microarray have attached probes specific for other soft tissue sarcomas deemed appropriate because of clinical differential diagnostic considerations. Also illustrated is the addition of a library of beads functionalized by the attachment of probes complementary to a stretch of nucleic acid present in specific soft tissue sarcomas, such as EWS and SYT. Beads functionalized by probes specific to other sarcomas being sought are not illustrated for the sake of clarity. Specific hybridization of the target chimeric transcript (SYT/SSX-1) [14] to the biochip containing bound probes for SSX-1 is identified by the attachment of beads with attached probes specific for SYT [FIG. 12B, right]. Detection of beads on the biochip containing bound SSX-1 probes indicates that the soft tissue tumor in question is a synovial sarcoma containing the chimeric transcript SYT/SSX-1. In this example, the biochip containing attached probes specific for ATF-1 (clear cell sarcoma of soft parts) [FIG. 12B, left] do not have attached beads because the chimeric transcript specific for clear cell sarcoma of soft parts (EWS/ATF-1) is not present.

3. Counting the Repeats in Repetitive DNA

Many hereditary diseases are caused by excessive lengthening of certain regions harboring a repetitive sequence. For instance, Huntington's disease, an invariably fatal disease, is caused by the presence of repeats of "CAG" in the Huntingtin gene located in chromosome 4 exceeding thirty six times (http://www.ncbi.nlm.nih.gov/entrez/dispomim.cgi?id=143100).

To measure the number of repeats in a person's Huntingtin gene, conventional methods employ PCR.

This invention simplifies the measurement of the number of repeats [FIG. 13]. Thus probes are designed to flank the invariable portions of the gene adjacent to the repeat sequence (http://www.ncbi.nlm.nih.gov/entrez/query.fcgi?cmd=Retrieve&db=nucleotide&list_uids=450395&dopt=GenBank). "Well"-bound probes differ in the number of repeats they carry in addition to the in-varying sequence flanking the repeat. The bead bound probes carry the in-varying region on the opposite side of the repeat and a fixed number of repeats. A person with a given number of repeats, e.g. 5 "CAG" repeats will have the two probes perfectly aligned end to end when hybridized if the well-bound probe contains 4 repeats and the bead-bound probe contains 1 repeat. Other wells containing well-bound probes measuring over 4 (e.g. 5 or more) or less than 4 (e.g. 3 or less), will hybridize but will not produce perfect alignment of the ends. Utilizing a DNA ligase (an enzyme that covalently links two strands of DNA aligned on a complementary strand and with the ends in close proximity), the two probes can be ligated covalently. Probes that have a combined number of repeats more than 5 will have an overhanging strand that is not ligateable with the other strand and so are probes with a combined repeats of less than 5 because of a big gap between the ends of the two probes. After the hybridization and ligation reactions, modification of the reaction conditions causes the probes and target to dissociate (melt), resulting in the absence of signals from biochips that have "well"-bound probes having other than exactly 4 CAG repeats.

In a heterozygous individual, two biochips will yield a positive signal, giving the repeat length of the two alleles, respectively. This invention thus enables rapid and accurate measurement of the number of CAG repeats in a person's Huntingtin gene.

This application is adaptable to any of the class of genetic diseases with varying repeat numbers as well as in the measurement of the number of repeats in microsatellite DNA and instability in the number of repeats in the inherited or acquired conditions of microsatellite instability.

Microsatellite profiling using this method can be used in paternity testing and forensic identification of human remains.

Figure 13A:
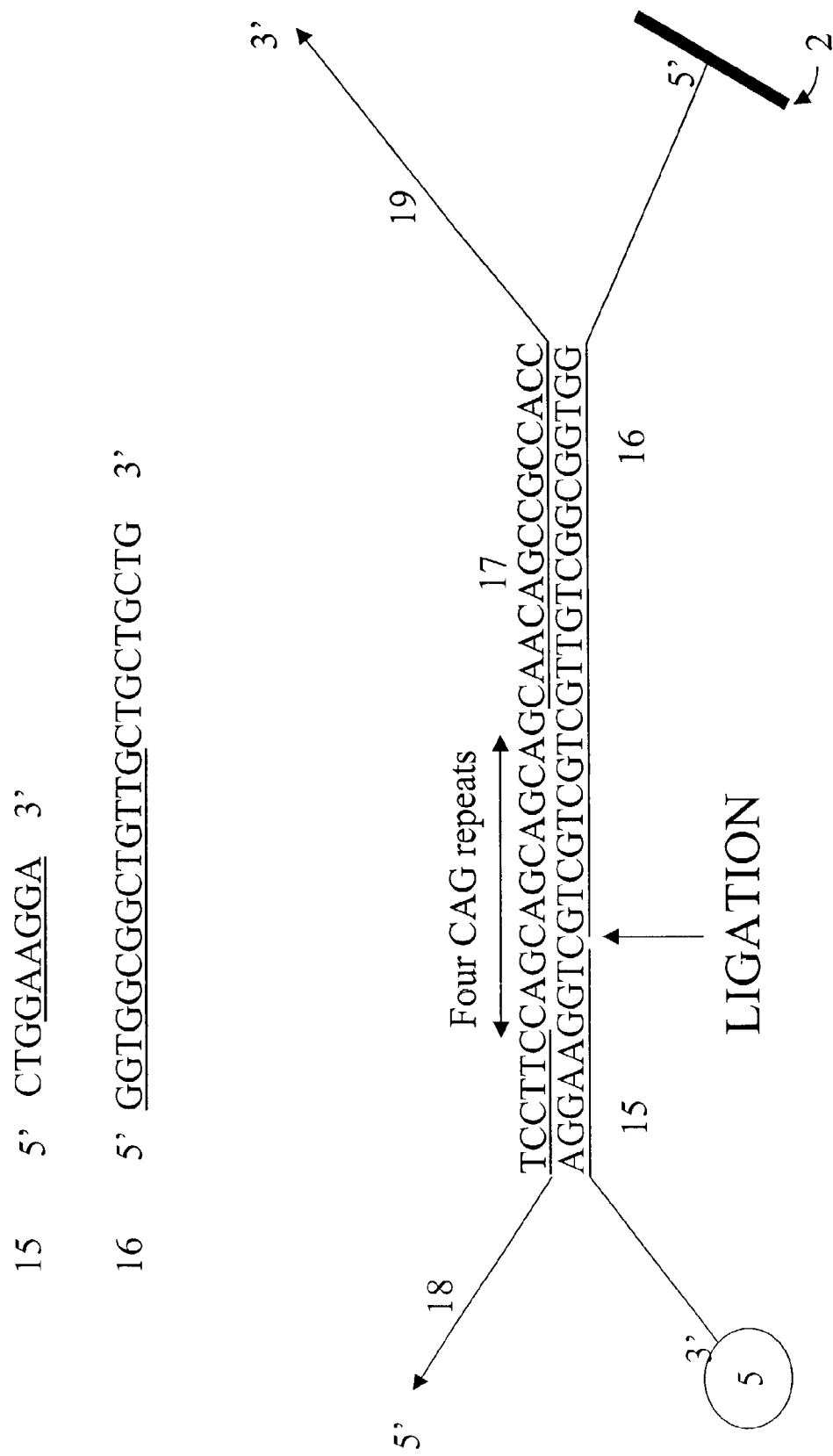
FIG. 13 depicts the concept behind the use of the biochip microarray and allele-specific oligonucleotide hybridization in the measurement of the number of repetitive elements in genomic DNA, in this illustration, Huntington's disease, FIG. 13A schematically depicts the design of the two probes (SEQ ID NOS 1 & 2) for the repeat region of the Huntingtin gene. The combined numbers of repeats in the probes matches that in the genomic DNA of a given patient. Ligation is possible after hybridization.
FIG. 13B schematically depicts another set of probes (SEQ ID NOS 3 & 2) that have a combined number of repeats that fall short of the exact number of repeats present in a given patient. No ligation of the two ends of the probes occurs.
FIG. 13C schematically depicts yet another set of probes (SEQ ID NOS 4 & 2) having a combined number of repeats in excess of the exact number of repeats present in a given patient, giving rise to overhanging probe and failure of ligation.

FIG. 13 depicts the above mentioned principles in the measurement of DNA repeats. The hypothetical Huntingtin gene in this example contains 4 CAG repeats. FIG. 13A shows that the bead bound probe [15] is designed to have the following sequence in the probing region: CTGGAAGGA and the "well"-bound probe [16] the following sequence in the probing region: GGTGGCGGCTGTTGCTGCTGCTG. (SEQ ID NO: 1). In the drawing, the top strand [17] is the target gene bearing four sets of "CAG" repeats in this particular patient. Only the regions complementary to the probes are depicted with the actual nucleotide sequence. The other ends (5' [18] and 3' [19]), are represented by arrows. The hybridized bead-bound [15] and well-bound probes [16,] are depicted using the same convention. The underlined parts of the probes (above the drawing) highlight the non-repeating portion flanking the repeat areas. In the drawing, the two probes have a combined number of repeats matching that of the target (four to be exact). Thus the 5' and 3' ends of these probes are brought together and can be ligated by an enzyme (DNA ligase).

Figure 13B:
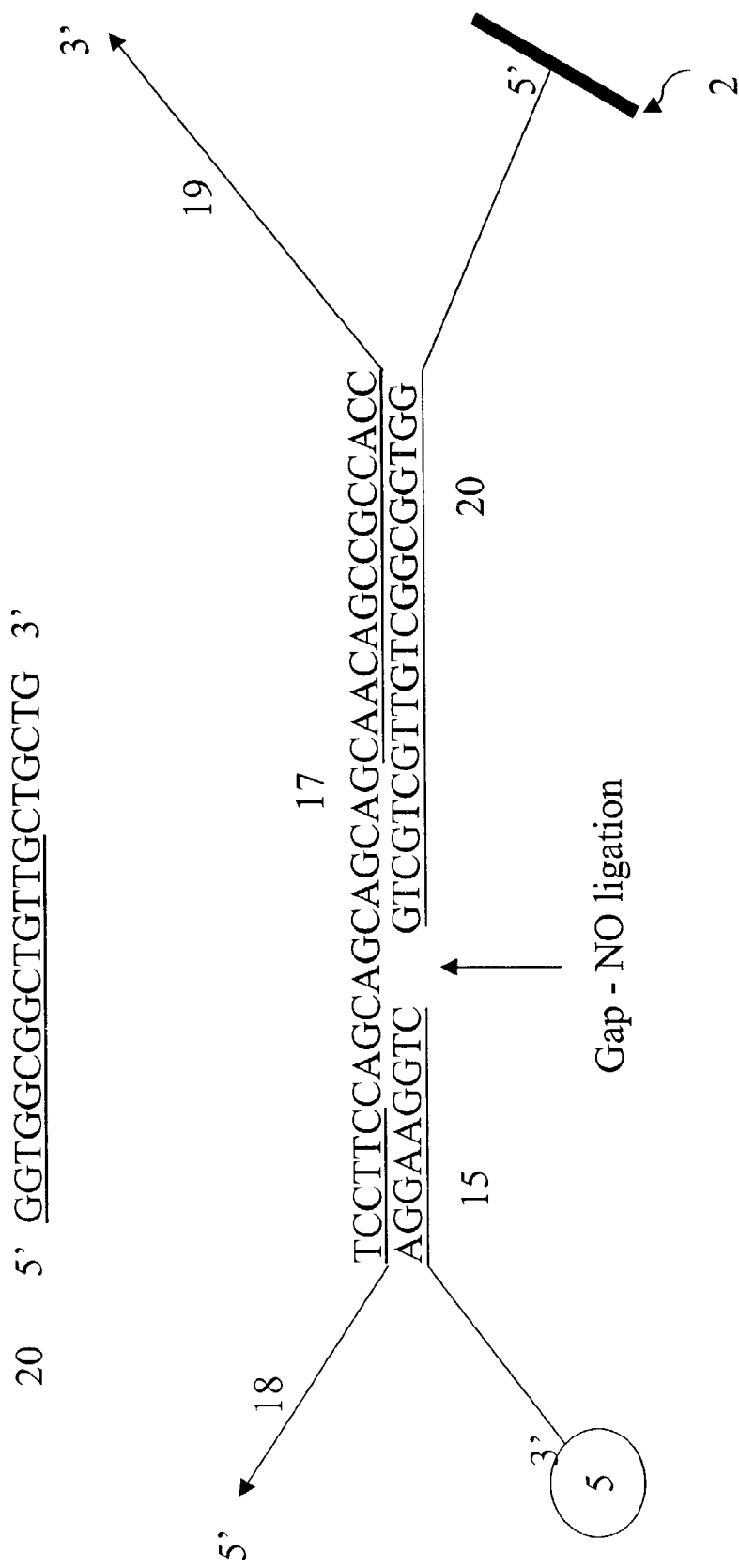

In FIG. 13B only the sequence of a different "well"-bound probe [20] is depicted, as the bead-bound probe is the same. This "well"-bound probe [20] is placed on another biochip on the same microarray. The "well"-bound probe [20] illustrated here has only two repeats, causing a gap to be present between the two probes upon hybridization with the target. The two probes cannot be ligated.

Figure 13C:
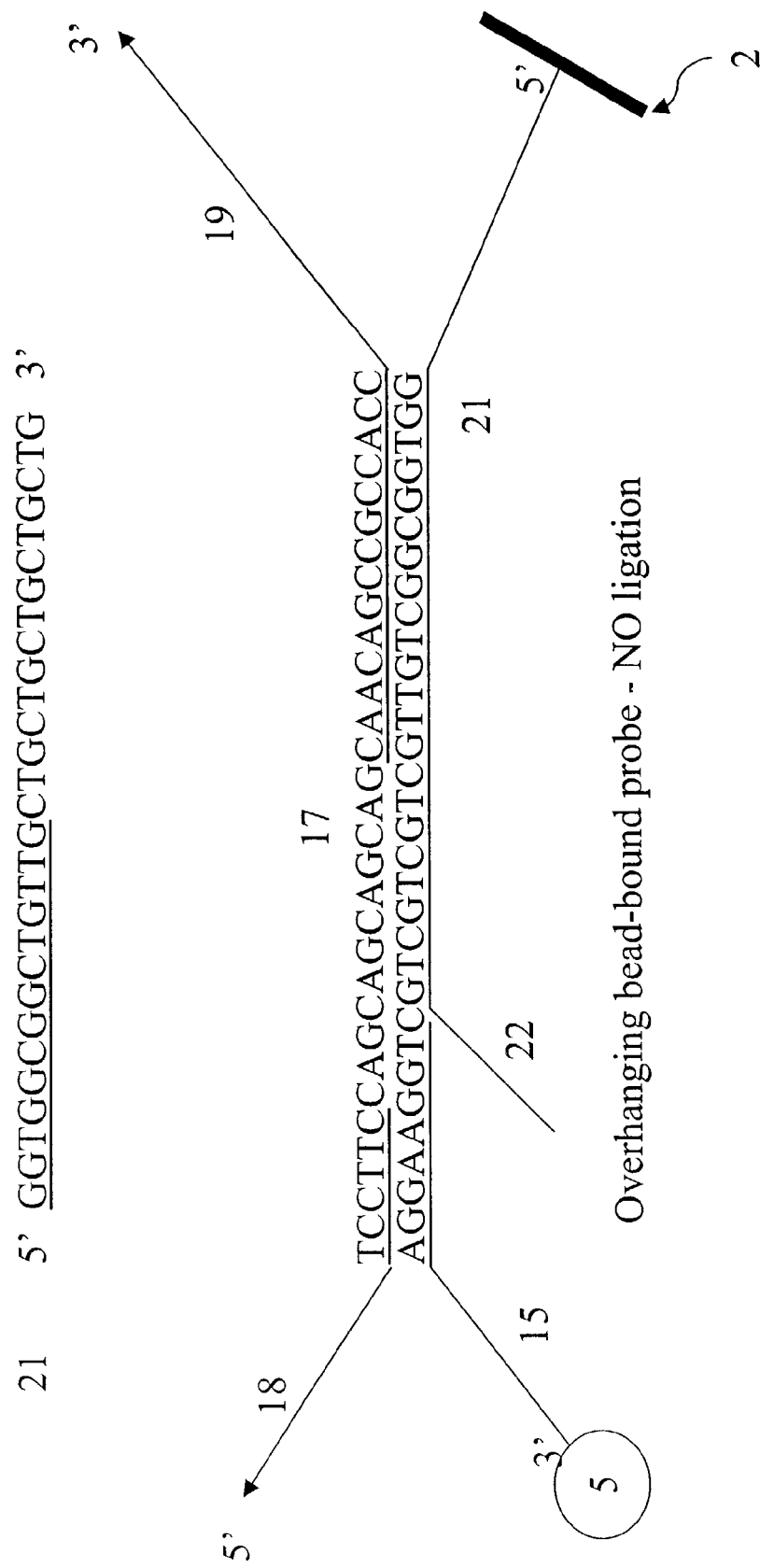
Figure 14A:
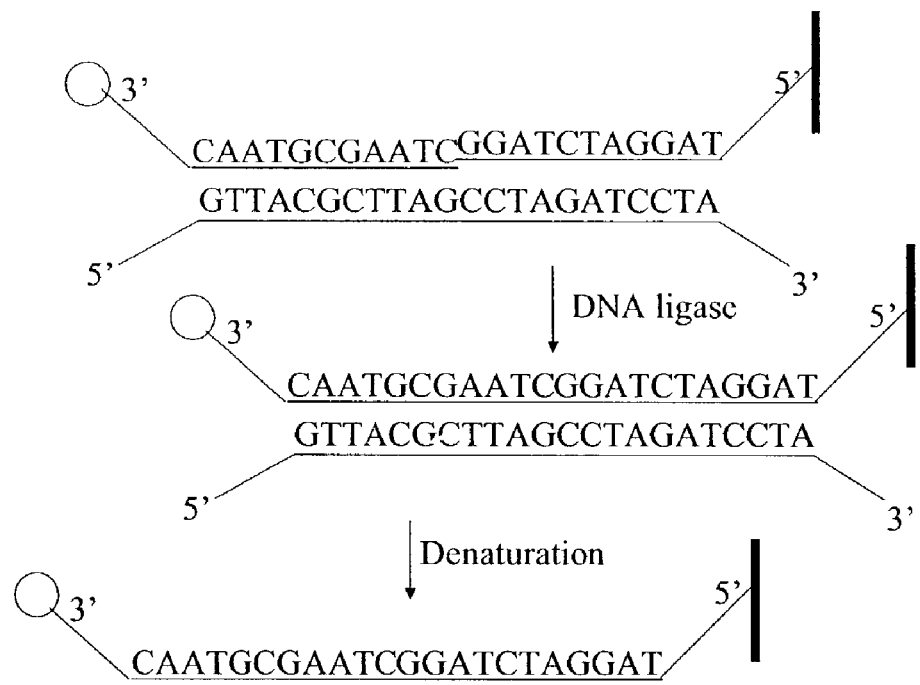
FIG. 14 illustrates the application of a similar design in the characterization of single nucleotide polymorphism (SNP) or mutation detection (SEQ ID NOS 5–7).
Figure 14B:
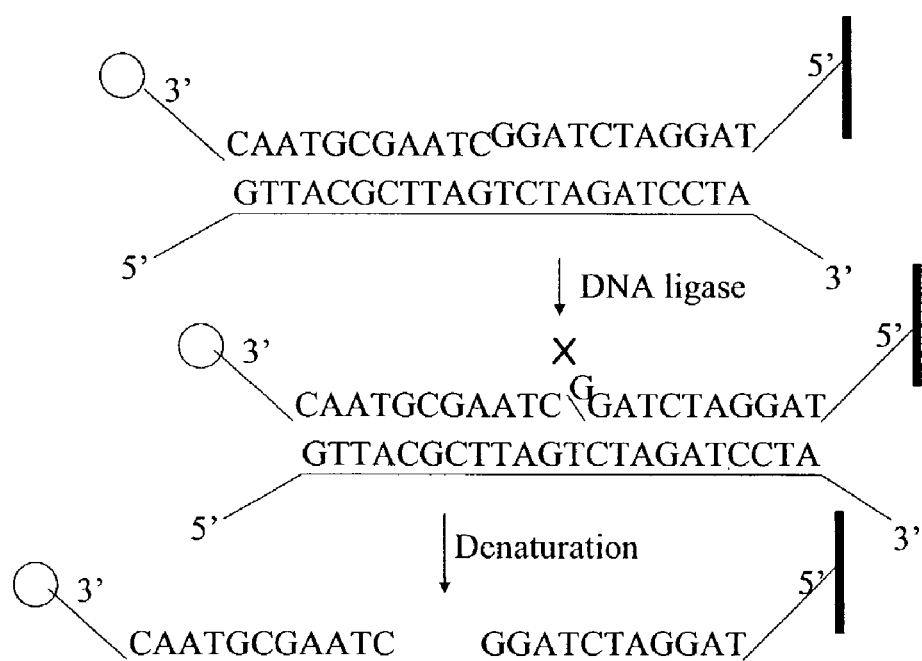
Figure 14C:
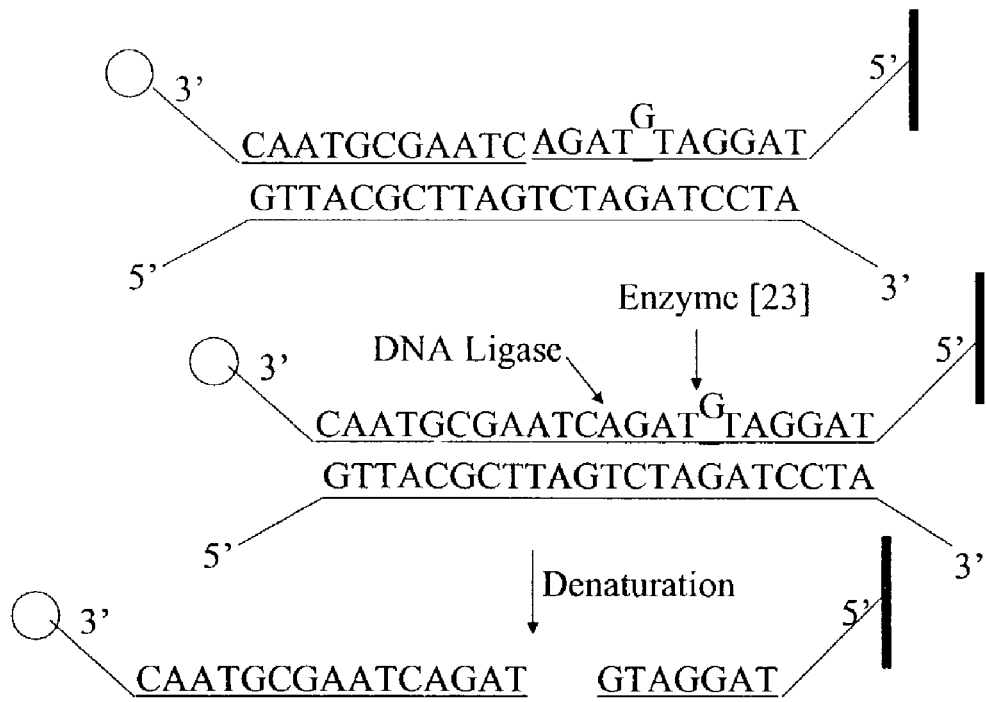
Figure 14D:
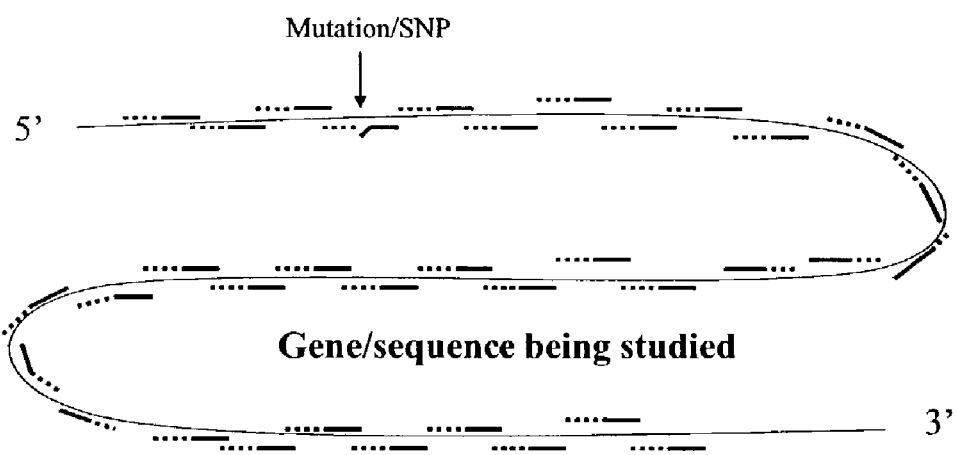
Figure 14E:
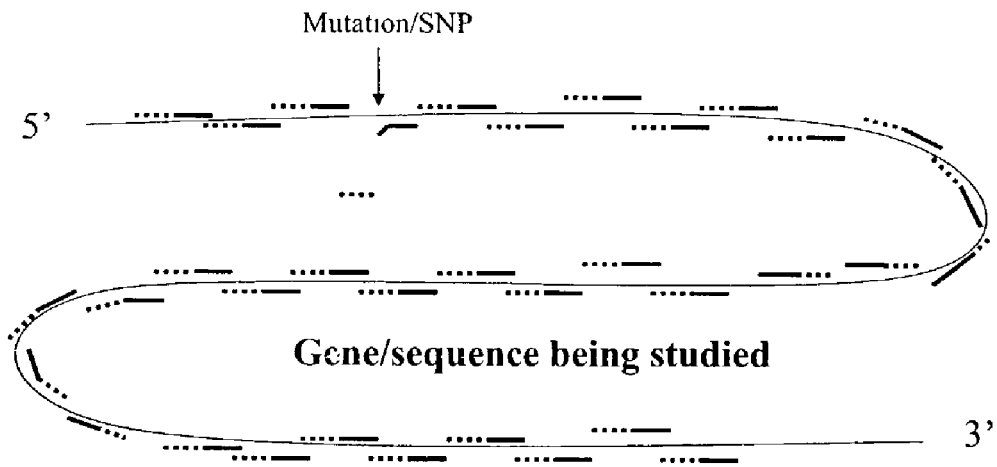
Figure 14F:
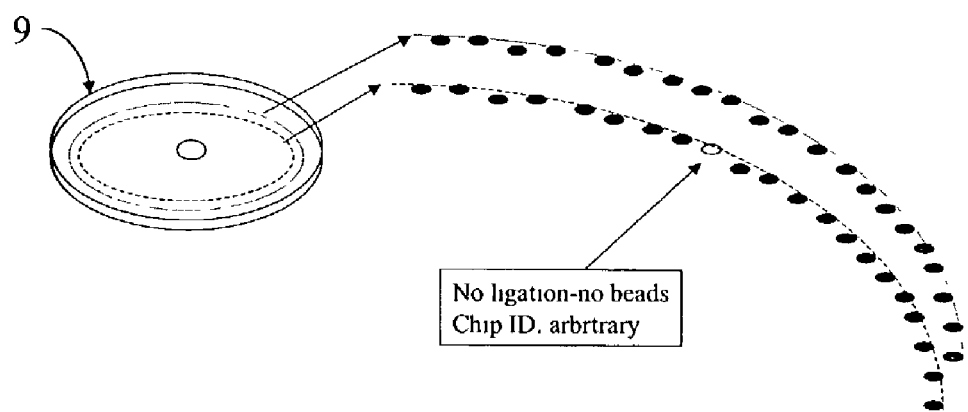

In FIG. 13C yet another "well"-bound probe [21] has too many repeats (5 in number). The excess portion therefore "overhangs" [22] after hybridization. Again there is no ligation.

4. Mutation Detection & SNP Profiling

Mutation detection is a means to discover that a given disease is handed down in the germ cells (hereditary).

The detection of single point mutations in genes (sometimes very large) by conventional methods that are based on amplification of areas of genes suffer from the disadvantage that large segments cannot be amplified and hence restricting the ability to economically and systematically studying a given person's gene for point mutations.

With this invention, pairs of probes ("well-bound and bead-bound) can be designed with knowledge of the sequence of unmutated genes (found in public databases). The pair of probes is designed to be complementary to consecutive stretches of the sequence. As many pairs are designed as necessary to cover the entire length of the gene being studied and the different "well"-bound probes attached to individual biochips, the region they are probing being stored in the unique identifier of the cassette.

In this way and with a special construct of the device to make it reusable, fast, economical and systematic study of gene mutation can be performed.

The same method can be used to define single nucleotide polymorphisms. The sequence of the gene is first determined. As many pairs of probes as needed to span the entire genetic sequence is designed, so that one of each pair hybridizes to one stretch of DNA and the other of a pair hybridizes to an adjacent sequence in such a way that the 5' end of one meets the 3' end of the other when both are hybridized to the DNA. One of each pair of probes is attached to specifically addressed biochips and the other to beads. Attachment of the bead to the biochip occurs after hybridization and ligation in an environment that discriminates single nucleotide mismatch, such as optimal sodium chloride concentration and/or temperature of annealing. To enhance the discrimination of single nucleotide mismatch, the addition of cleavase, mismatch repair enzymes or other enzymes that detect and cleave double-stranded DNA with mismatch, can be included. Pairs of probes are designed so that when hybridized to the gene being studied, they are arranged in tandem, with adjacent pairs showing some degree of overlap, thus achieving the effect of interrogating the entire sequence of the gene without omitting any areas, introns and exons alike. The addition of DNA ligase causes ligation of each pair if there is no mismatch between either of the two probes (thus resulting in hybridization of both probes), and the target gene. Adjacent pairs do not ligate because of overlap of the sequences. In this way, the biochip without attached beads after the reaction gives the location of any SNP. This "biochip-tagged" stretch of DNA can then be amplified by one of the methods of nucleic acid amplification and sequenced to reveal the nature of the SNP.

For allelic discrimination in a heterozygous individual, modification of the "digital truncation test" is used (Traverso et. al.). A 96-well microtiter plate is used. Genomic DNA is diluted and aliquots dispensed to each well. The dilution is such that in each well, only one or two gene of interest is present. Each well is subjected to a multiplex PCR amplification designed to represent the entire gene in segments of amplifiable length, so that at the end of the reaction, many copies of each segment of the gene results. Random selection of some reaction products is then used as "target" in separate interrogations using the biochip microarray for SNP or mutation.

Owing to the presence of only one allele in some of the "targets", allelic discrimination can be achieved.

Alternative to genomic DNA, the mRNA of the gene can be interrogated in a similar fashion.

With further adaptation of the methodology, LOH and chromosomal aneuploidy can be identified readily with the biochip microarray. Known microsatellite markers for a chromosomal region are utilized in hybridization reactions of normal tissue and tumor tissue to compare their presence or absence, which in the case of loss of one of two heterozygous alleles, indicates LOH. This, in combination with mutation detection is a powerful tool for the study of putative tumor suppressor genes. Chromosomal aneuploidy in tumor is also readily detected by microsatellite markers and together with the prior applications form a set of important tools for the genetic profiling and diagnosis of cancer based on a few cancer cells collected either from exfoliated cells (such as urine, cervix) or by percutaneous fine needle aspiration.

FIG. 14 depicts the use of this invention to identify the location of SNP or point-mutation/deletion/insertion. As many pairs of probes (attached to biochip and beads) as necessary to cover the entire length of a given gene are designed. If both probes in a pair align with the 5' and 3' ends in proximity to each other after hybridization to the genomic DNA, ligation by DNA ligase will result in the binding of beads to the biochip (FIG. 14A). If a SNP is present at the ligation site, no ligation occurs (FIG. 14B). If one of the probes has a single nucleotide mismatch elsewhere (FIG. 14C), then no hybridization occurs in a stringent environment within a specific temperature (Tm) or saline concentration window. Addition of an enzyme [23] that recognizes and cleaves double-stranded DNA with a mismatch, such as cleavase or mismatch repair enzyme, will cleave the probe with a mismatch and also prevent joining of the two probes. The result is the absence of beads on the biochip interrogating the segment of DNA sequence containing the SNP (FIGS. 14D, 14E & 14F). FIG. 14F illustrates the final result on such a microarray, with the biochip without bound beads indicating the stretch of nucleic acid on which the SNP or mutation is located. This stretch ("biochip-tagged") can then be amplified in another reaction and sequenced to yield the SNP.

5. Quantitative Gene Expression

In scientific research, scientists frequently need to study gene expression. In a multicellular organism, cells carrying the same set of genes specialize to takes up numerous bodily functions such as covering the body surface (integument or skin), absorbing fluids and electrolytes (intestines), and interacting with the outside world (nervous system). As the result, the cells need tools, which are expressed in these specialized cells that are not expressed in the other differentiated cells. Until now, gene expression is studied by fluorescent probes or other means, individually or employing the microarray, on which are printed or otherwise attached molecular probes which hybridize with the messenger RNA (or cDNA) and create a qualitative result of whether the targets are present or absent. Needless to say, these microarrays do not have the ability to quantify the mRNA, which may be expressed but at a low level. Low-level expression may also be important because we do not know that low-level expression is necessarily synonymous with few proteins being made since protein concentration in a cell is dynamic, and represents equilibrium between production and destruction.

With this invention, quantification of mRNA and the corresponding protein is simple, as described in "Quantification (Molecular Assay)" above.

Figure 10B:
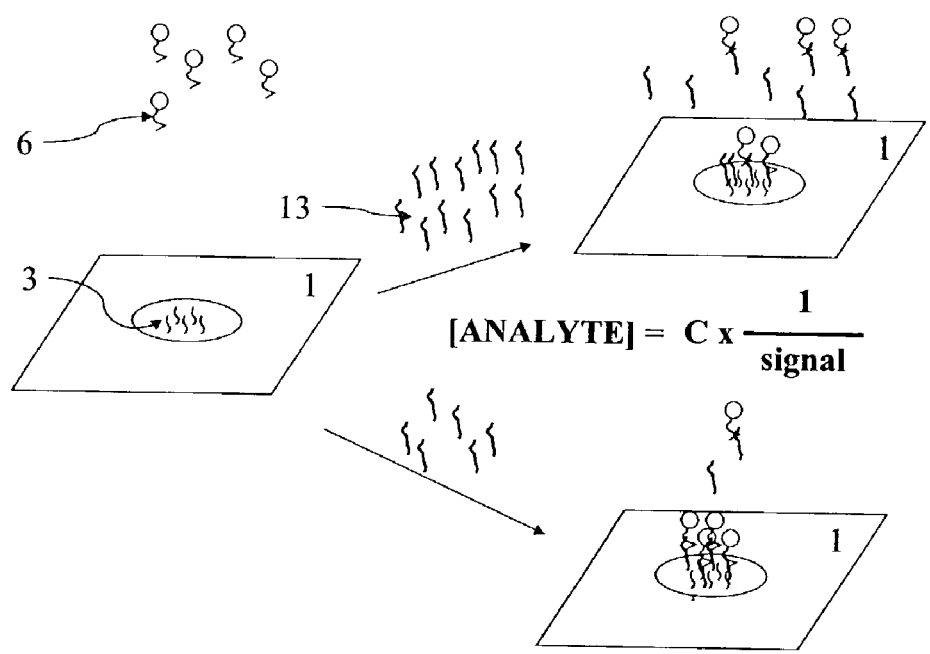
Figure 15A:
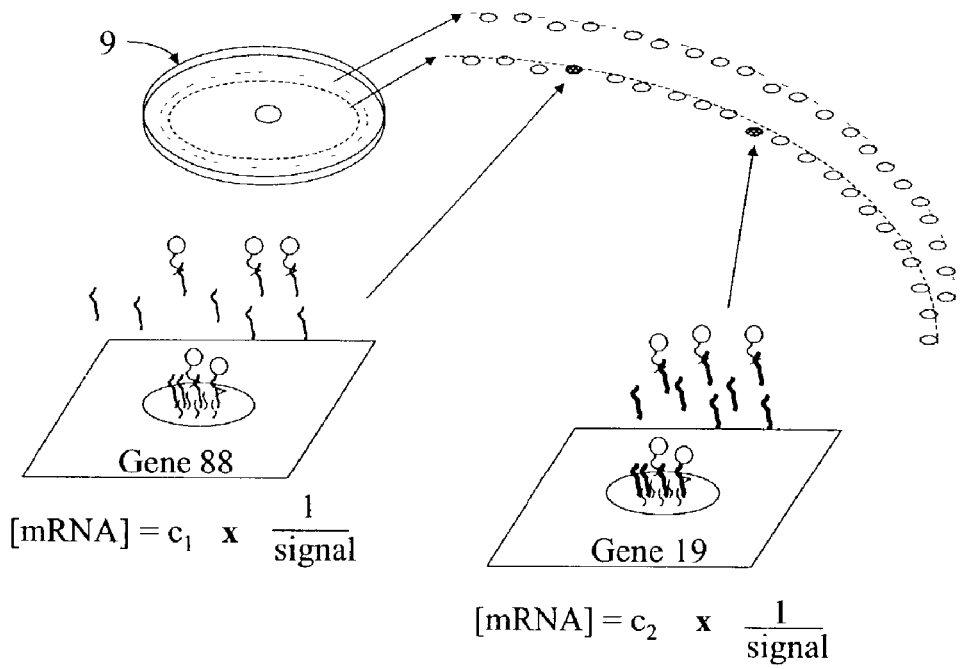
FIG. 15 depicts the application of the second method of competitive binding assay in the measurement of mRNA levels and protein concentrations.
Figure 15B:
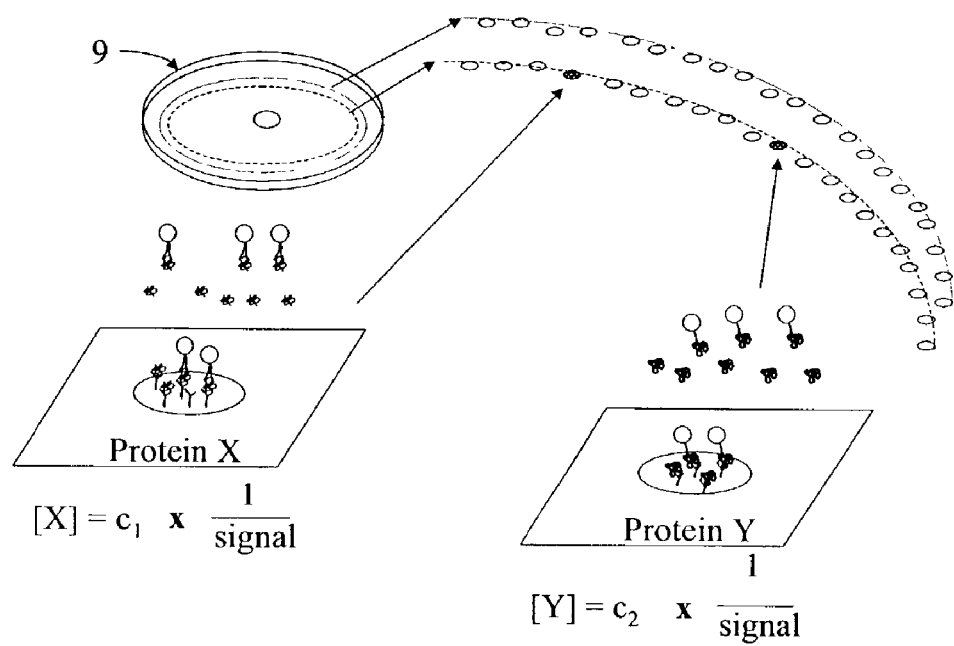

FIG. 15 depicts the harnessing of the power of the microarray and the principle of competitive binding in the measurement of the concentration of mRNA (FIG. 15A) and protein (FIG. 15B), respectively. The method of assaying is described in FIG. 10 and in the text.

6. Proteomics

The proteome of a single celled organism or the proteomes of various cells of a multicellular organism contains hundreds of thousands of proteins. To study the interaction of these proteins among themselves and other molecules is a daunting task. This invention embodies a method which provides an opportunity to rapidly and economically study protein-protein and protein-other molecule interactions by virtual of specific physical interactions between these molecules. In FIG. 16, the microarray is depicted in the investigation of protein-protein interaction. The various proteins of a cell or organism are first isolated and deposited on specific locations on the biochip microarray. Next, each one of these various proteins is bound separately to the surface of ferromagnetic beads. When the beads are sequentially introduced into the biochip microarray in a suitable carrier fluid under suitable conditions, protein-protein interactions can be rapidly studied. A database of such interactions can be built up with considerable speed. Proteins that interact with a given protein, the functions of which are known, are highly likely to participate in the same and similar cellular functions (guilt by association). Modification of the reaction environment by the addition or depletion of certain small molecules can conceivably add information to the complexity of protein-protein interactions.

In another embodiment, specific antibodies are raised against the entire proteome (for example, of plasma) and specifically addressed onto the biochip microarray. Another set of specific antibodies against alternative epitopes of the proteome is raised. The biochip can then be adapted to measure the concentration of the proteins in a proteome using the principle of competitive binding as outlined above.

7. Drug Discovery & Screening

Figure 17:
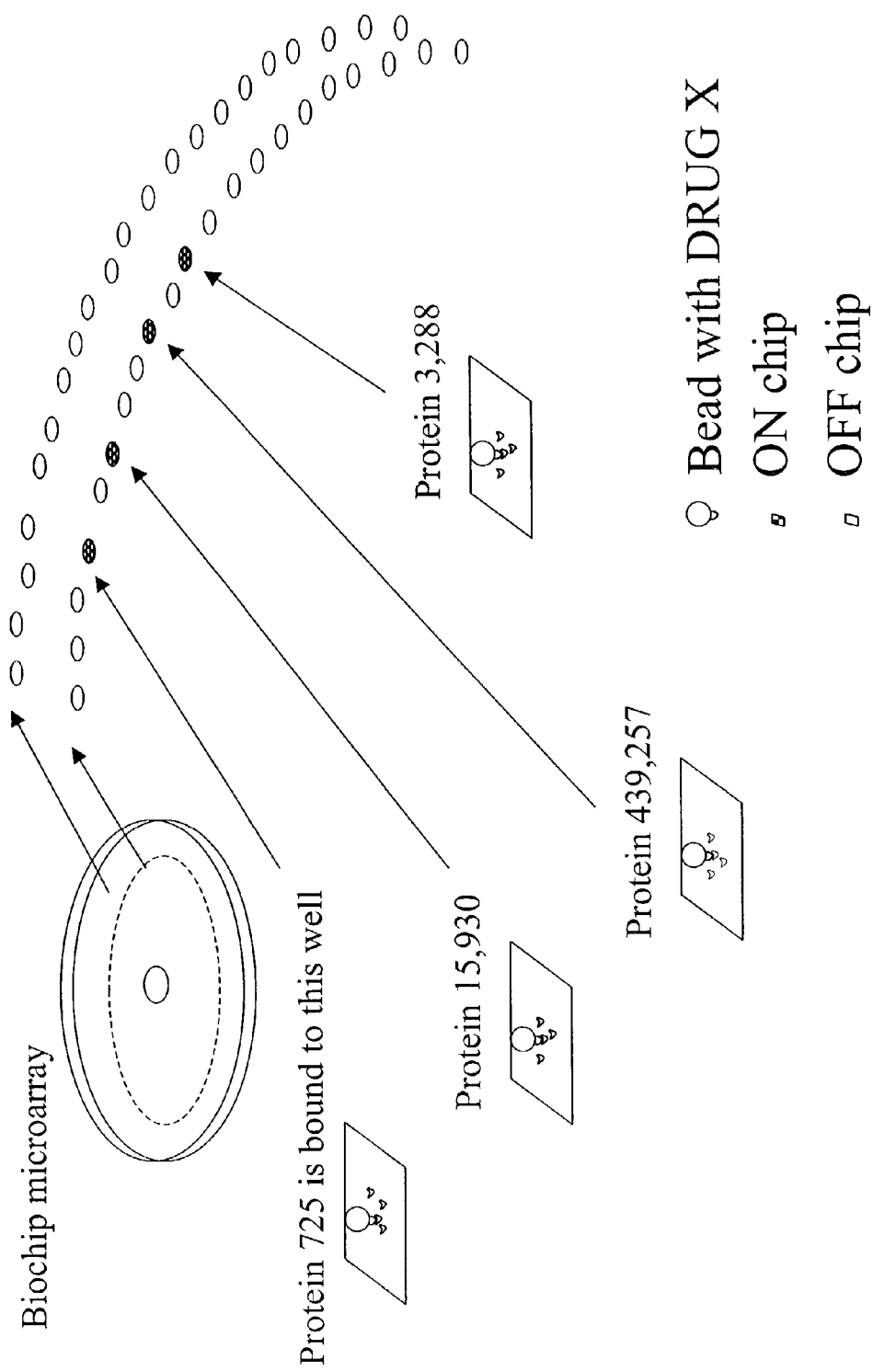
FIG. 17 depicts the use of the microarray in drug screening. Drugs that show strong affinity to specific proteins can be identified.

The previous model can also be used to study drug interactions with the proteome if drug molecules, rather than proteins, are attached to the beads. This is because drugs with pharmacological or toxicological activities often show physical interactions or bindings with certain proteins. Drug distribution in various body compartments is also affected by binding with various proteins, determining not only the distribution but also the pharmacokinetics of the drug. By sequentially applying beads with specific drugs to the biochip microarray, proteins showing affinity with the drugs can be identified with ease. Drug screening for pharmacological activities and toxicities can be performed rapidly. In FIG. 17, the microarray is depicted in a similar configuration as FIG. 16, this time in the investigation of drug-protein interactions as a basis of drug screening. Instead of a library of individual proteins bound to beads, the proteins are replaced by drug molecules that are to be screened for possible pharmacological value or toxicological implications.

More Applications

There are many possible applications of this invention. An exhaustive list is impossible. A few more examples are given below.

EXAMPLE ONE

Early Diagnosis of Tuberculous Infection

The ribosomal ribonucleic acid (rRNA) of Mycobacterium tuberculosis (the cause of human tuberculosis) is the target of detection in the AMPLIFIED™ Mycobacterium Tuberculosis Direct Test (References 9–18).

Whereas amplification is required in the above test (Transcription Mediated Amplification (TMA)), the current invention requires the simple process of breakdown of the bacterial cell wall. This invention can detect as little as a few copies of the bacterial rRNA. No prior amplification is necessary.

EXAMPLE TWO

Early Diagnosis of Acute Myocardial Infarction

The timely laboratory diagnosis of an acute myocardial infarction (heart attack) is potentially lifesaving because therapeutic interventions can be instituted. These interventions are not without their own risks and mandate an accurate test.

Until now, tests are either not sensitive enough or non-specific. For example, the earliest indicator of myocardial infarction is elevation of serum myoglobin, which is detectable at 6 hours after infarction (References 12–15). However, myoglobin is also present in skeletal muscle and its elevation is not specific for myocardial injury, requiring confirmation by a second assay of serum troponin T (http://www.roche.com/diagnostics/news/1998/981127a.html), a marker that is elevated later than myoglobin.

The ability to detect minute quantities of cardiac troponin T in the earliest stages of an acute myocardial infarction requires both specificity and sensitivity. This is now possible using this invention.

In this application, the principle of competitive binding is employed as described in "Quantification" above. The analyte would be cardiac troponin T and the two probes would be antibodies raised against cardiac troponin T. The antibodies should bind to two different epitopes on the cardiac troponin T molecule with avidity and without interference of each other (epitopes not too close as to interfere with the binding of the two antibodies). In addition to being able to detect previously undetectable quantities of circulating cardiac troponin T early in an episode of acute myocardial infarction (which probably exists much sooner than 6 hours after an acute myocardial infarction), the application also permits quantification of the serum level of this protein (calibration of the instrument can be readily achieved by serial dilutions of known concentrations of cardiac troponin T).

EXAMPLE THREE

Measurement of Viral Load

Many diseases have a viral cause. An example is HIV (infection by the human immunodeficiency virus). Whereas the disease is controllable by anti-viral agents, these are all very expensive. Because the virus is prone to mutation, not all patients are responsive to the same drug(s) at different periods. Monitoring the viral load is one way to determine drug efficacy and disease status.

Using this method, viral load study is rendered highly accurate, simple, fast and economical.

The principles of assay are described above.

Any virus can be studied using this method, provided the genetic sequence is known.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

REFERENCES

1. Immink K A S (1998). The compact disc story. Journal of the audio engineering society 46, 458–465.
2. Zhang D Y, Brandwein M, Hsuih T C H, Li Hongbo. Amplification of target-specific, ligation-dependent circular probe. Gene 211 (1998) 277–285.
3. Zhang D Y, Brandwein M, Hsuih T, Li H B. Ramification amplification: a novel isothermal DNA amplification method. Molecular Diagnosis 6 (2001):141–150.
4. Zhang D Y, Zhang W, Li X, Konomi Y. Detection of rare DNA targets by isothermal ramification amplification. Gene 274 (2001) 209–216.
5. Umek R M, Lin S W, Vielmetter J, Terbrueggen R H, Irvine B, Yu C J, Kayyem J F, Yowanto H, Blackburn G F, Farkas D H, Chen Y. Electronic detection of nucleic acids: a versatile platform for molecular diagnostics. J Mol Diagn 2002;3:74–84.
6. Park S J, Taton T A, Mirkin C A. Array-based electrical detection of DNA with nanoparticle probes. Science 2002 Feb. 22;295(5559):1503–6.
7. Baselt D R, Lee G U, Natesan M, Metzger S W, Sheehan P E, Colton R J. A biosensor based on magnetoresistance technology. Biosensors & Bioelectronics 13,731–739(1998).
8. Baselt D R, Lee G U, Hansen K M, Chrisey L A, Colton R J. A High-Sensitivity Micromachined Biosensor. Proc. IEEE 85(4), 672–680 (1997).
9. Behr, M. A., S. A. Warren, H. Salamon, P. C. Hopewell, A. Ponce de Leon, C. L. Daley, and P. M. Small. 1999. Transmission of Mycobacterium tuberculosis from patients smear-negative for acid-fast bacilli. Lancet. 353: 444–449.
10. Bermann, J. S., G. Yuoh, G. Fish and G. L. Woods. 1999. Clinical evaluation of the enhanced Gen-Probe Amplified Mycobacterium Tuberculosis Direct Test for rapid diagnosis of tuberculosis in prison inmates. J. Clin. Microbiol. 37:1419–1425.
11. Bermann, J. S. and G. L. Woods. 1999. Enhanced mycobacterium tuberculosis direct test for detection of M. tuberculosis complex in positive ESP II broth cultures of nonrespiratory specimens Diag. Microbiol. Infect. Dis. 35: 245–248.
12. Chedore,P. and F. B. Jamieson. 1999. Routine use of the Gen-Probe MTD2 amplification test for detection of Mycobacterium tuberculosis in clinical specimens in a large public health mycobacteriology laboratory. Diag. Microbiol. Infect. Dis. 35:185–191.
13. Della-Latta, P. and S. Whittier. 1998. Comprehensive evaluation of performance, laboratory application, and clinical usefulness of two direct amplification technologies for the detection of Mycobacterium tuberculosis complex. Am. J. Clin. Pathol. 110:301–310.
14. Della-Latta, P. and Vivian Jonas. 1999. Inhibitory effect of Alpha-Tec XPR-Plus Phosphate Buffer on the enhanced Gen-Probe Amplified Mycobacterium Tuberculosis Direct Test. J. Clin. Microbiol. 37:1234–1235.
15. Gamboa, F., G. Fernandez, E. Padilla, J. M. Manterola, J. Ionca, P. J. Cardona, L. Matas, and V. Ausina. 1998. Comparative Evaluation of initial and new versions of the Gen-Probe Amplified Mycobacterium Tuberculosis Direct Test for direct detection of Mycobacterium tuberculosis in respiratory and nonrespiratory specimens. J. Clin. Microbiol. 36:684–689.
16. Moore, D. F. and Curry, J. I. 1999. Reduction in turnaround time for detection and identification of Mycobacterium tuberculosis from pulmonary specimens using nucleic acid amplification tests. Presented at the 99th General Meeting of the American Society of Microbiology. Chicago, Ill.
17. Piersimoni, C., A. Callegaro, C. Scarparo, V. Penati, D. Nista, S. Bornigia, C. Lacchini, M. Scagnelli, G. Santini, and G. De Sio. 1998. Comparative evaluation of the new Gen-Probe Mycobacterium tuberculosis Direct Test and the semiautomated Abbott LCx Mycobacterium tuberculosis assay for direct detection of Mycobacterium tuberculosis complex in respiratory and extrapulmonary specimens. J. Clin. Microbiol. 36:3601–3604.
18. Wang, S. X. and L.Tay. 1999. Evaluation of three nucleic acid amplification methods for direct detection of Mycobacterium tuberculosis complex in respiratory specimens. J. Clin. Microbiol. 37:1932–1934.
19. Bakker A J, Loelemey M J, Gorgels J P, von Vlies B, Smits R, Tijssen J G, Haagen F D: Troponin T and myoglobin at admission: value of early diagnosis of acute myocardial infarction. Eur Heart J 1994.
20. De Winter R J, Koster R W, Sturk A, Sanders G T: Value of myoglobin, troponin T, and CK-MB Mass in ruling out an acute myocardial infarction in the emergency room. Circulation. 1995; 92: 3401–3407.
21. Hamm C W, Katus H A: New biochemical markers for myocardial cell injury. Current Opinion in Cardiology, 1995; 10: 355–360.
22. Tucker J F, Collins R A, Anderson A J, Hess M, Farley I M, Hagemann D A, Harkins H J, Zwicke D: Value of serial myoglobin levels in the early diagnosis of patients admitted for acute myocardial infarction. Ann Emerg Med 1994; 24: 704–708.
23. P. Brown et al., "Bovine spongiform encephalopathy and variant Creutzfeldt-Jakob disease: background, evolution, and current concerns," Emerging Infectious Diseases, 7[1]:6–16, Jan.–Feb. 2001.
24. J. Bieschke et al., "Ultra-sensitive detection of pathological prion protein aggregates by dual-color scanning for intensely fluorescent targets," Proceedings of the National Academy of Sciences (PNAS), 97:5468–73, 2000.
25. M. R. Scott et al., "Identification of a prion protein epitope modulating transmission of bovine spongiform encephalopathy to transgenic mice, " PNAS, 94:14279–84, 1997.
26. "The Evaluation of Tests for the Diagnosis of Transmissible Spongiform Encephalopathy in Bovines," European Commission, Directorate General XXIV, Consumer Policy and Consumer Health Protection, Jul. 8, 1999.
27. Safar J, Wille H, Itri V, Groth D, Serban H, Torchia M, Cohen F E, Prusiner S B. "Eight prion strains have PrPSc molecules with different conformations," Nature Medicine, 4:1157–65, 1998.
28. BSE Surveillance, U.S. Department of Agriculture, Animal and Plant Health Inspection Service. Internet publication link: http://www.aphis.usda.gov/oa/bse/bse-survey.html.
29. Traverso G., Shuber A., Levin B., Johnson C., Olsson L., Schoetz D. J. Jr., Hamilton S. R., Boynton K., Kinzler K. W., Vogelstein B. Detection of APC Mutations in Fecal DNA from Patients with Colorectal Tumors. N Engl J Med 2002; 346:311–320, Jan. 31, 2002.

U.S. PATENT DOCUMENTS

U.S. Ser. No. 08/505,628 July, 1995 Lee, et.al.
U.S. Ser. No. 09/997,059 November, 2001 Tong, Sun-wing
U.S. Pat. No. 3,742,174 June, 1973 Harnden, Jr.
U.S. Pat. No. 3,742,178 June, 1973 Harnden, Jr.
U.S. Pat. No. 3,742,179 June, 1973 Harnden, Jr.
U.S. Pat. No. 4,315,150 February, 1982 Darringer, et al.
U.S. Pat. No. 4,965,188 October, 1990 Mullis, et. al.
U.S. Pat. No. 5,445,970 August, 1995 Rohr, Thomas E.
U.S. Pat. No. 5,445,971 August, 1995 Rohr, Thomas E.
U.S. Pat. No. 5,876,924 March, 1999 Zhang, et. al.
U.S. Pat. No. 5,942,391 August, 1999 Zhang, et. al.
U.S. Pat. No. 6,320,169 November, 2001 Clothier
U.S. Pat. No. 3,833,769 September, 1974 Compaan, Klass
U.S. Pat. No. 3,397,364 August, 1968 Crandall, CL

I claim:

1. A method of detecting the presence or absence of a molecular target in a sample, comprising:
    forming bead bound probes by attaching to a bead a first molecular probe capable of attaching to one part of the molecular target;
    forming support-bound probes by attaching to a support at a predefined area a second molecular probe capable of attaching to a second part of the molecular target, wherein said support is an optical disk having reflecting and non-reflecting binary features thereon and has an axis of rotation;
    introducing the sample to the bead-bound probes and the support-bound probes and allowing binding of the molecular target to said bead-bound probes and said support-bound probes so that the molecular target is sandwiched between the support and the beads, and the beads are attached on the support;
    aggregating beads that are not bound to the support around beads that are attached on the support;
    rotating the support about its axis of rotation; and
    determining the presence or absence of beads at the predefined area on the rotating support, wherein the detection of the beads on the rotating support indicates the presence of the molecular target in the sample.

2. The method of claim 1 wherein at least two different molecular targets are detected in the sample.

3. The method of claim 1 wherein one molecular target is detected at least twice.

4. The method of claim 1 further comprising a step of removing any unbound beads before detecting the presence of beads on the support.

5. The method of claim 1 wherein the amount of bead-bound probes is in excess of the amount of molecular target in the sample.

6. The method of claim 1 wherein, the step of aggregating beads comprises the steps of:
    choosing demagnetized dark, non-reflective beads for making said bead-bound probes;
    applying a magnetic field to magnetize said beads after the binding of said molecular target to said bead-bound probes and said support-bound probes;
    initiating the aggregation of said magnetized beads; and
    removing beads that are not attached to said support.

7. The method of claim 6 wherein the step of detecting the presence of aggregated magnetized beads comprises:
    applying a fluctuating magnetic field to said aggregates of beads;
    measuring the acoustic signal produced by said aggregates of beads.

8. The method of claim 1 wherein said step of aggregating comprises the steps of:
    binding a chemical moiety onto the beads;
    adding a chemical reagent with multiple identical binding sites that bind with an affinity and specificity to the chemical moiety after said binding of said molecular target to said bead-bound probes and said support-bound probes so as to chemically bind and aggregate the beads on the support.

9. The method of claim 8 wherein the chemical moiety is biotin, and the chemical reagent is avidin or streptavidin.

10. The method of claim 8 wherein the chemical moiety is biotin, and the chemical reagent is IgM anti-biotin antibody.

11. The method of claim 8 wherein the chemical moiety is Staphylococcal protein A or Streptococcal protein G, and the chemical reagent is immunoglobulin dimers or multimers.

12. The method of claim 6 wherein the step of detecting the presence of the beads on the support comprises:
    providing a support having a light reflective surface to form a reflective support;
    directing laser light onto the reflective support;
    monitoring the reflection of the laser light to detect the attenuation of the laser light by the non-reflective beads on a reflective area of the reflective support to thereby detect the presence of the non-reflective beads on the reflective support.

13. The method of claim 1 wherein the beads comprise a metallic component, and said step of detecting the presence of beads on the support comprises:
  subjecting the beads to an external magnetic field to induce an opposing magnetic field by the beads;
  detecting the presence of the induced magnetic field to thereby detect the presence of beads on the support.

14. The method of claim 1 wherein the beads comprises a ferromagnetic component, and said step of detecting the presence of beads on the support comprises:
  magnetic inductive heating of the beads on the support; and
  detecting the infrared radiation emitted by the heated beads to thereby detect the presence of beads on the support.

15. The method of claim 14 wherein the radiation is detected by an infrared sensor.

16. The method of claim 14 wherein the beads are heated by a rapidly alternating magnetic field.

17. The method of claim 14 wherein a thermoluminescent agent is added to the beads on the support, and the radiation emitted by the heated beads causes the thermoluminescent agent to emit light which is detected by a photodiode.

18. The method of claim 14 wherein a chemiluminescent or bioluminescent agent is added to the surroundings of the beads on the support, and the thermal energy produced by the heated beads cause increase in the rate of chemical reaction and the intensity of emitted light, which is detected by a photodiode.

19. The method of claim 17 wherein the emitted light is used to pump a laser, thereby amplifying the emitted light signal.

20. The method of claim 18 wherein the emitted light is used to pump a laser, thereby amplifying the emitted light signal.

21. The method of claim 1 wherein the support contains machine-readable information relating to at least the second molecular probe, wherein the information is contained in a discrete region of the support that is located on the support surface having the second molecular probe attached thereto.

22. The method of claim 21, wherein the machine-readable information comprises the identity of at least one of the molecular probes attached to the support.

23. The method of claim 21, wherein the machine-readable information comprises information relating to a process by which the plurality of molecular probes is attached to the support surface.

24. The method of claim 21, wherein the machine-readable information comprises information relating to experimental conditions associated with a use of the plurality of the molecular probes.

25. The method of claim 21, wherein the machine-readable information comprises information relating to the results of an experiment associated with a use of the plurality of the molecular probes.

26. The method of claim 21, wherein the machine-readable information is digital.

27. The method of claim 1 further comprising the step of determining the concentration of the molecular target in the sample based on the difference in the amount of detectable beads present on the support in the presence of at least two different concentrations of the molecular target.

28. The method of claim 1 wherein the beads are reflective and the step of detecting the presence of the beads on the support comprises:
  providing a support having a light reflective surface;
  directing laser light onto the reflective support; and
  monitoring the reflection of the laser light to detect the reflection of the laser light by the reflective beads on a non-reflective area of the support to thereby detect the presence of the beads on the support.

29. The method of claim 1 wherein the beads are reflective.

30. The method of claim 29 wherein the step of detecting the presence of the beads on the support comprises;
  providing a support having a light non-reflective surface to form a non-reflecting support;
  directing laser light onto the non-reflective support; and
  monitoring the reflection of the laser light to detect the reflection of the laser light by the reflective beads on a non-reflective area of the non-reflective support to thereby detect the presence of the reflective beads on the non-reflective support.

31. A method of detecting the presence or absence of a molecular target in a sample, comprising:
  forming bead bound probes by attaching to a bead a first molecular probe capable of attaching to one part of the molecular target;
  forming support-bound probes by attaching to a support at a predefined area a second molecular probe capable of attaching to a second part of the molecular target, wherein said support has an axis of rotation;
  introducing the sample to the bead-bound probes and the support-bound probes and allowing binding of the molecular target to said bead-bound probes and said support-bound probes so that the molecular target is sandwiched between the support and the beads, and the beads are attached on the support;
  rotating the support about its axis of rotation; and
  determining the presence or absence of beads at the predefined area on the rotating support, wherein the detection of the beads on the rotating support indicates the presence of the molecular target in the sample;
  wherein the beads are reflective, and the step of detecting the presence of the beads on the support comprises:
  providing a support having a light non-reflective surface to form a non-reflective support;
  directing laser light onto the non-reflective support; and
  monitoring the reflection of the laser light to detect the reflection of the laser light by the reflective beads on a non-reflective area of the non-reflective support to thereby detect the presence of the reflective beads on the non-reflective support.

32. A method of detecting the presence or absence of a molecular target in a sample, comprising:
  forming bead bound probes by attaching to a bead a first molecular probe capable of attaching to one part of the molecular target;
  forming support-bound probes by attaching to a support at a predefined area a second molecular probe capable of attaching to a second part of the molecular target, wherein said support has an axis of rotation;
  introducing the sample to the bead-bound probes and the support-bound probes and allowing binding of the molecular target to said bead-bound probes and said support-bound probes so that the molecular target is sandwiched between the support and the beads, and the beads are attached on the support;
  rotating the support about its axis of rotation; and
  determining the presence or absence of beads at the predefined area on the rotating support, wherein the detection of the beads on the rotating support indicates the presence of the molecular target in the sample;

wherein the beads comprise a metallic component, and said step of detecting the presence of beads on the support comprises:

subjecting the beads to an external magnetic field to induce an opposing magnetic field by the beads; and detecting the presence of the induced magnetic field to thereby detect the presence of beads on the support.

33. A method of detecting the presence or absence of a molecular target in a sample, comprising:

forming bead bound probes by attaching to a bead a first molecular probe capable of attaching to one part of the molecular target;

forming support-bound probes by attaching to a support at a predefined area a second molecular probe capable of attaching to a second part of the molecular target, wherein said support has an axis of rotation;

introducing the sample to the bead-bound probes and the support-bound probes and allowing binding of the molecular target to said bead-bound probes and said support-bound probes so that the molecular target is sandwiched between the support and the beads, and the beads are attached on the support;

rotating the support about its axis of rotation; and determining the presence or absence of beads at the predefined area on the rotating support, wherein the detection of the beads on the rotating support indicates the presence of the molecular target in the sample;

wherein the beads comprises a ferromagnetic component, and said step of detecting the presence of beads on the support comprises:

magnetic inductive heating of the beads on the support; and detecting the infrared radiation emitted by the heated beads to thereby detect the presence of beads on the support.

34. A method of detecting the presence or absence of a molecular target in a sample, comprising:

forming bead bound probes by attaching to a bead a first molecular probe capable of attaching to one part of the molecular target;

forming support-bound probes by attaching to a support at a predefined area a second molecular probe capable of attaching to a second part of the molecular target, wherein said support has an axis of rotation;

introducing the sample to the bead-bound probes and the support-bound probes and allowing binding of the molecular target to said bead-bound probes and said support-bound probes so that the molecular target is sandwiched between the support and the beads, and the beads are attached on the support;

aggregating beads that are not bound to the support around beads that are attached on the support;

rotating the support about its axis of rotation; and determining the presence or absence of beads at the predefined area on the rotating support, wherein the detection of the beads on the rotating support indicates the presence of the molecular target in the sample.

* * * * *